(12) United States Patent
McKerracher

(10) Patent No.: US 7,491,692 B2
(45) Date of Patent: Feb. 17, 2009

(54) METHODS FOR MAKING AND DELIVERING RHO-ANTAGONIST TISSUE ADHESIVE FORMULATIONS TO THE INJURED MAMMALIAN CENTRAL AND PERIPHERAL NERVOUS SYSTEMS AND USES THEREOF

(76) Inventor: Lisa McKerracher, 600, de la Savoyane, Ile des Soeurs, Quebec (CA) H3E 1Y7

(*) Notice: Subject to any disclaimer, the term of this patent is extended or adjusted under 35 U.S.C. 154(b) by 820 days.

(21) Appl. No.: 10/718,598

(22) Filed: Nov. 24, 2003

(65) Prior Publication Data

US 2004/0121011 A1   Jun. 24, 2004

Related U.S. Application Data

(62) Division of application No. 09/725,906, filed on Nov. 30, 2000, now Pat. No. 7,141,428.

(30) Foreign Application Priority Data

Nov. 2, 2000 (CA) .................... 2325765
Nov. 29, 2000 (CA) .................... 2325842

(51) Int. Cl.
A61K 38/00 (2006.01)
A61K 38/16 (2006.01)
A61K 38/45 (2006.01)
C07K 14/00 (2006.01)
C07D 471/04 (2006.01)

(52) U.S. Cl. .............. 514/2; 424/198.1; 424/94.5; 530/350; 435/810; 514/303; 546/119

(58) Field of Classification Search ........... None
See application file for complete search history.

(56) References Cited

U.S. PATENT DOCUMENTS

| | | | |
|---|---|---|---|
| 4,359,049 A | 11/1982 | Redl et al. | |
| 4,631,055 A * | 12/1986 | Redl et al. | ........... 604/82 |
| 4,874,368 A | 10/1989 | Miller et al. | |
| 4,978,336 A | 12/1990 | Capozzl et al. | |
| 4,997,834 A | 3/1991 | Muro et al. | |
| 5,900,408 A | 5/1999 | Block et al. | |
| 5,922,356 A | 7/1999 | Koseki et al. | |
| 5,945,115 A | 8/1999 | Dunn et al. | |
| 5,989,215 A | 11/1999 | Delmotte et al. | |
| 6,036,955 A | 3/2000 | Thorper et al. | |
| 6,047,861 A | 4/2000 | Vidal et al. | |
| 6,117,425 A | 9/2000 | MacPhee et al. | |
| 6,121,422 A | 9/2000 | Zimmerman et al. | |
| 6,124,273 A | 9/2000 | Drohan et al. | |
| 6,218,410 B1 | 4/2001 | Uehata et al. | |
| 7,141,428 B2 * | 11/2006 | McKerracher | ........... 424/239.1 |

FOREIGN PATENT DOCUMENTS

| | | |
|---|---|---|
| CA | 2300878 | 2/1999 |
| CA | 2304981 | 5/1999 |
| EP | 0956865 | 2/1998 |
| WO | WO98/06433 | 2/1998 |

OTHER PUBLICATIONS

Zigmond, M.J., editor, 1999, Fundamental Neuroscience, Academic Press, pp. 526-543.*
Houweling et al., Exp. Neurology 153: 49-59 (1998).
Masuda-Nakagawa, L., et al, 1993, PNAS, 90: 4966-4970.
Ramon-Cueto et al. Neuron 25:425-435 (2000).
Hauser, et al, 1993, J. Bacteriol., 175(22): 7260-7268.
Moriishi, et al, 1993, Infection and Immunity, 61(12): 5309-5314.
Omelchenko, et al, 2003, PNAS, 100(19): 10788-1079.
Spronk, et al, 2004, Thrombosis J., 2: 12-21.
Ten Berg, et al, 2001, Curr. Control. Trials Cardiovasc. Med., 2: 129-140.
Ishizaki, et al, 2000, Mol. Pharmacol., 57: 976-983.
Winton, et al, 2002, J. Biol. Chem., 277(36): 32820-32829.
Taniguchi-Sidle, et al, 1992, J. Biol. Chem, 287(1): 635-643.
Itoh, et al, 1999, Nature Medicine, 5(2): 221-225.
Blazso, et al, 2004, Phytother. Res., 18(7): 579-581.
Itano, et al, 2002, Proc. Natl. Acad. Sci., 99(6): 3609-3614.
Saito, et al, 1995, FEBS, 371: 105-109.
Boston life sciences, Sep. 6, 2000 Press release.
Aguayo, et al., J. Exp. Biol.95:231-40 (1981).
Schwab et al. Annu. Rev. Neurosci. 16:565-595 (1993).
Schnell and Schwab Nature 343:269-272 (1990).
Weibel, et al. Brain Res 642:259-266 (1994).
Ramer, et al. Nature 403:312-316 (2000).
Liu, et al. J. Neurosci 19:4370-87 (1999).
Blesh, et al., J. Neurosci 19:3556-66 (1999).
Schnell, et al., Nature 367:170-173 (1994).
Neuman, Neuron 2383-91 (1999).
Cai, et al., Neuron 22:89-101 (1999).
Lehmann, et al. J. Neurosci 19:7537-7547 (1999).
Li, et al., J. Neurosci res. 46:404-414 (1996).
Fan, et al., J. Cell Biol. 121:867-878 (1993).
Tigyi, et al., Journal of Neurochemistry 66:537-548 (1996).
Kuhn, et al. J. Neurosci 19:1965-1975 (1999).
Jin and Strittmatter, J. Neurosci 17:6256-6263 (1997).
Zheng and Li, J. Biol. Chem. 272:4671-4679 (1999).
van Leeuwen, et al. J. Cell Biol. 139:797-807 (1997).
Nobes and Hall, Cell 1995,81:53-62 (1995).
Laudanna, et al., Science 271:981-983 (1996).
Hannigan, et al., Nature 379:91-96 (1996).
Kuhn, et al., J. Neurobiol. 37:524-540 (1998).

(Continued)

*Primary Examiner*—Elizabeth C. Kemmerer
*Assistant Examiner*—Sandra Wegert

(57) ABSTRACT

The present invention provides methods for making, delivering and using formulations that combine a therapeutically active agent(s) (such as for example a Rho antagonist(s)) and a flowable carrier component capable of forming a therapeutically acceptable matrix in vivo (such as for example tissue adhesives), to injured nerves to promote repair and regeneration and regrowth of injured (mammalian) neuronal cells, e.g. for facilitating axon growth at a desired lesion site. Preferred active agents are known Rho antagonists such as for example C3, chimeric C3 proteins, etc. or substances selected from among known trans-4-amino(alkyl)-1-pyridylcarbamoylcyclohexane compounds or Rho kinase inhibitors. The system for example may deliver an antagonist(s) in a tissue adhesive such as, for example, a fibrin glue or a collagen gel to create a delivery matrix in situ. A kit and methods of stimulating neuronal regeneration are also included.

12 Claims, 8 Drawing Sheets

OTHER PUBLICATIONS

Hall, Ann. Rev. Cell. Biol. 10:31-54 (1996).
Kozma, et al., Molec. Cell. Biol. 17:1201-1211 (1997).
Albertinazzi, et al. J. Cell. Biol. 142:815-825 (1998).
Huthchens, et al. Molec. Biol. Cell 8:481-500 (1997).
Daniels, et al., EMBO Journal 17:754-764 (1998).
Sebok, et al. J. Neurochem 73:949-960 (1999).
Lang, et al., EMBO Journal 15:510-519 (1996).
Dong, et al., J. Biol. Chem 273:22554-22562 (1998).
Renaudin, et al., J, Neurosci Res. 55:458-471 (1998).
Dillon and Feigh, Methods in Enzymology: Small GTPases and their regulators Part. B.256:174-184 (1995).
Kimura and Schubert, Journal of Cell Biology 116:777-783 (1992).
Keino-Masu, et al., Cell. 87:175-185 (1996).
Matsui, et al., EMBO J. 15:2208-2216 (1996).
Matsui, et al., J. Cell Biol. 140:647-657 (1998).
Ishizaki, FEBS Lett. 404:118-124 (1997).
Vaheri, et al., Curr. Opin. Cell. Biol. 9:659-666 (1997).
Goslin, et al., J. Cell Biol. 109:1621-1631 (1989).
Hirose, et al., J. Cell Biol. 141:1625-1636 (1998).
Bito, Neuron 26:431-441 (2000).
Ishizali, et al., Molecular Pharacology 57:976-983 3 (2000).
Uehata, et al., Nature 389:990-994 (1997).
Somlyo, Nature 389:908-911 (1997).
Mansour-Robaey 1994 PNAS 91:1632-1636.
Guest, J. Neurosci Res. 50:888-905 (1997).
Verge, et al., Journal of Neuroscience 15;2081-2096 (1995).
Cheng, et al., Science, 273:510-513 (1996).
Joosten, J, Neurosci Res. 41:481-490 (1995).
Kennedy, et al., Cell. 78:425-435 (1994).
McKerracher, et al., Molec. Neurobiol. 12:95-116 (1996).
Diekmann and Hall, in Methods in Enzymology vol. 256 part B 207-215 (1995).
Xu, et al., Exp. Neurol 134:261-272 (1996).
Guest Exp. Neurol. 148:502-522 (1997).
Tuszynsli, et al., Cell Transplant 7:187-96 (1998).
Liu, et al., Exp. J. Neurosci. 19:4370-4387 (1999).
Tuszynski, et al., Exp. Neurol 126:1-14 (1994).
Nakahara, et al., Cell Transplant 5:191-204 (1996).
Diener and Bregman J. Neurosci 18:779-793 (1998).
Bregman, Exp. Neurol 123:2-16 (1993).
Lazarov-Spiegler, et al., FASEB J. 110:1296-1302 (1996).
McDonald, et al., Nat. Med. 5:1410-2 (1999).
Li, et al. Science 277:2000-2002 (1997).
Ramon-Cueto, et al., J. Neurosci 18:3803-15 (1998).
Herbert J. Biomed. Mater Res. 40:551-559 (1998).
Janknecht, et al., Proc. Natl. Acad. Sci. USA 88, 8972 (1981).
Beattie, Basso and Breshnahan, J. Neurotrauama 12:1-20 (1995).
Ridley and Hall, Cell. 70:389-399 (1992).
Popoff, et al., Nucl. Acid. Ress.18:1291 EMBL accession No. X511464 (1990).
Methods in Enzymology, vol. 256, Part B., Eds.; W.E. Balch, C.H. Der, and A. Hall. Academic Press, 1995.

* cited by examiner

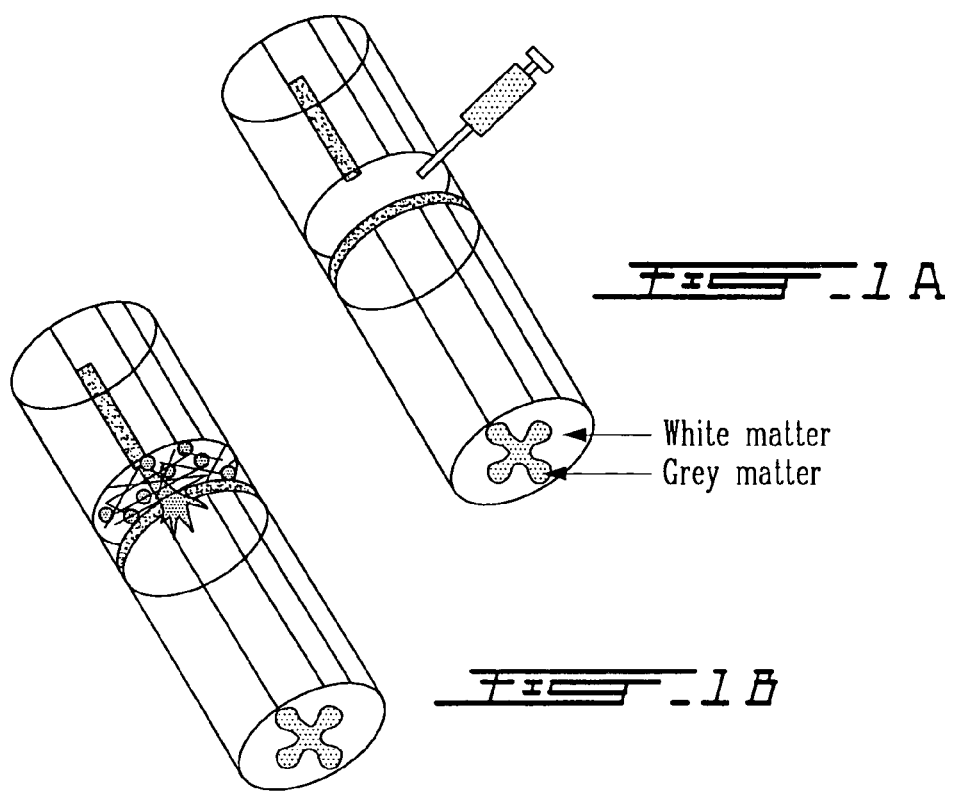
FIG-1A
— White matter
— Grey matter
FIG-1B
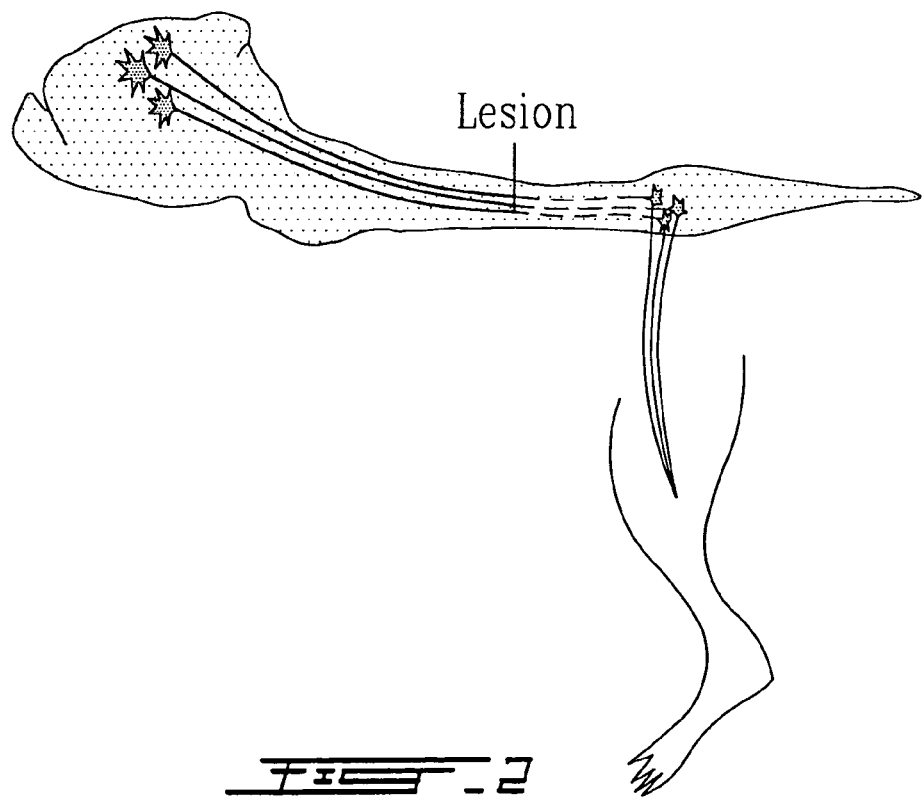
Lesion
FIG-2

Lesion

SEQUENCE LISTING

```
<160> NUMBER OF SEQ ID NOS: 3

<210> SEQ ID NO 1
<211> LENGTH: 726
<212> TYPE: DNA
<213> ORGANISM: Clostridium botulinum

<400> SEQUENCE: 1
gtggcgaccc ttcccaaatc ggatctggtt ccgcgtggat cctctagagt cgacctgcag      60
gcatgcaatg cttattccat taatcaaaag gcttattcaa atacttacca ggagtttact     120
aatattgatc aagcaaaagc ttggggtaat gctcagtata aaaagtatgg actaagcaaa     180
tcagaaaaag aagctatagt atcatatact aaaagcgcta gtgaaataaa tggaaagcta     240
agacaaaata agggagttat caatggattt ccttcaaatt aataaaaca agttgaactt     300 ttagataaat cttttaataa aatgaagacc cctgaaaata ttatgttatt tagaggcgac     360
gaccctgctt atttaggaac agaatttcaa aacactcttc ttaattcaaa tggtacaatt     420
aataaaacgg cttttgaaaa ggctaaagct aagtttttaa ataaagatag acttgaatat     480
ggatatatta gtacttcatt aatgaatgtt tctcaatttg caggaagacc aattattaca     540
aaatttaaag tagcaaaagg ctcaaaggca ggatatattg accctattag tgcttttcag     600
ggacaacttg aaatgttgct tcctagacat agtacttatc atatagacga tatgagattg     660
tcttctgatg gtaaacaaat aataattaca gcaacaatga tgggcacagc tatcaatcct     720
aaataa                                                                 726

<210> SEQ ID NO 2
<211> LENGTH: 690
<212> TYPE: DNA
<213> ORGANISM: Clostridium botulinum

<400> SEQUENCE: 2
ggatcctcta gagtcgacct gcaggcatgc aatgcttatt ccattaatca aaaggcttat      60
tcaaatactt accaggagtt tactaatatt gatcaagcaa aagcttgggg taatgctcag     120
tataaaaagt atggactaag caaatcagaa aaagaagcta tagtatcata tactaaaagc     180
gctagtgaaa taaatggaaa gctaagacaa aataagggag ttatcaatgg atttccttca     240
aatttaataa aacaagttga acttttagat aaatctttta ataaaatgaa gacccctgaa     300
aatattatgt tatttagagg cgacgaccct gcttatttag gaacagaatt tcaaaacact     360
cttcttaatt caaatggtac aattaataaa acggcttttg aaaaggctaa agctaagttt     420
ttaaataaag atagacttga atatggatat attagtactt cattaatgaa tgtttctcaa     480
tttgcaggaa gaccaattat tacaaaattt aaagtagcaa aaggctcaaa ggcaggatat     540
attgacccta ttagtgcttt tcagggacaa cttgaaatgt tgcttcctag acatagtact     600
tatcatatag acgatatgag attgtcttct gatggtaaac aaataataat tacagcaaca     660
```

```
atgatgggca cagctatcaa tcctaaataa                                           690

<210> SEQ ID NO 3
<211> LENGTH: 229
<212> TYPE: PRT
<213> ORGANISM: Clostridium botulinum

<400> SEQUENCE: 3

Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys
225
```

METHODS FOR MAKING AND DELIVERING RHO-ANTAGONIST TISSUE ADHESIVE FORMULATIONS TO THE INJURED MAMMALIAN CENTRAL AND PERIPHERAL NERVOUS SYSTEMS AND USES THEREOF

This application is a divisional of U.S. patent application Ser. No. 09/725,906, filed Nov. 30, 2000 now U.S. Pat. No. 7,141,428.

The present invention provides methods for making, delivering and using formulations that combine a therapeutically active agent(s) (such as for example a Rho antagonist(s)) and a flowable carrier component capable of forming a therapeutically acceptable matrix in vivo (such as for example tissue adhesives), to injured nerves to promote repair and regeneration and regrowth of injured mammalian neuronal cells, e.g. for facilitating axon growth at a desired lesion site active agents are known Rho antagonists such as for example C3, chimeric C3 proteins, etc. (see blow) or substances selected from among known trans-4-amino(alkyl)-1-pyridylcarbamoylcyclohexane compounds (also see below) or Rho kinase inhibitors. The system for example may deliver an antagonist(s) in a tissue adhesive such as for example, a fibrin glue or a collagen gel to create a delivery matrix in situ. A kit and methods of stimulating neuronal regeneration are also included.

FIELD OF THE INVENTION

The present invention pertains to the field of mammalian nervous system repair (e.g. repair of a central nervous system (CNS) lesion site or a peripheral nervous system (PNS) lesion site), axon regeneration and axon sprouting. The present invention in particular relates to a method of delivery of C3 or other Rho antagonists to repair damage in the nervous system. The invention also pertains to use of the delivery system for toxicity testing of compounds applied to the injured CNS. (i.e. to a central nervous system (CNS) lesion site or a peripheral nervous system (PNS) lesion site).

In the following by way of example only reference will generally be made to axon growth at a central nervous system (CNS) lesion site.

BACKGROUND

Traumatic injury of the spinal cord results in permanent functional impairment. Most of the deficits associated with spinal cord injury result from the loss of axons that are damaged in the central nervous system (CNS). Similarly, other diseases of the CNS are associated with axonal loss and retraction, such as stroke, HIV dementia, prion diseases, Parkinson's disease, Alzheimer's disease, multiple sclerosis and glaucoma. Common to all of these diseases is the loss of axonal connections with their targets, and the ability to stimulate growth of axons from the affected or diseased neuronal population would improve recovery of lost neurological functions. For example, following a white matter stroke, axons are damaged and lost, even though the neuronal cell bodies are alive. Treatments that are effective in eliciting sprouting from injured axons are equally effective in treating some types of stroke (Boston life sciences, Sep. 6, 2000 Press release). Similarly, although the following discussion will generally relate to delivery of Rho antagonists, etc. to a traumatically damaged nervous system, this invention also pertains to damage from unknown causes, such as during multiple sclerosis, HIV dementia, Parkinson's disease, Alzheimer's disease, prion diseases or other diseases of the CNS were axons are damaged in the CNS environment.

It has been proposed to use various agents to stimulate regeneration of cut axons, i.e. nerve lesions. Please see for example Canadian patent application Nos. 2,304,981 (McKerracher et al) and 2,300,878 (Strittmatter). These document propose the use of known Rho antagonists such as for example C3, chimeric C3 proteins, etc. (see blow) as well as substances selected from among known trans-4-amino (alkyl)-1-pyridylcarbamoylcyclohexane compounds (also see below) or Rho kinase inhibitors for use in the regeneration of axons.

Several major advances in our understanding of axon regeneration have led to the ability to stimulate some axon regeneration and functional repair in animal models of spinal cord injury. In the 1980's experiments by Aguayo and colleagues to use peripheral nerve grafts that were inserted into the brain or spinal cord showed that CNS neurons have the capacity to regrow, and these studies highlighted that diverse classes of CNS neurons have the potential to regenerate when given a permissive growth environment (Aguayo, et al. (1981) J Exp Biol. 95:231-40). However, this technique cannot be used to rewire the complex circuitry of the CNS. Another major advance in our understanding of axon regeneration in the central nervous system was the discovery by Schwab and colleagues that the CNS environment did not simply lack growth promoting molecules, but that growth inhibitory molecules existed to block axon growth (Schwab, et al. (1993) Annu. Rev. Neurosci. 16:565-595). Long distance regeneration in the CNS by blocking growth inhibitory molecules with antibodies was first achieved in juvenile rats by neutralization of inhibitory protein activity with the IN-1 antibody in spinal cord (Schnell and Schwab (1990) Nature. 343:269-272) and optic nerve (Weibel, et al. (1994) Brain Res. 642:259-266). However, this technique suffers from the problem that only a single growth inhibitory protein is targeted, and delivery by the application of hybridoma cells or by infusing antibodies with pumps. There have been investigations on the use of growth factors to promote regeneration in the CNS, some with notable success (Ramer, et al. (2000) Nature. 403:312-316, Liu, et al. (1999) J Neurosci. 19:4370-87, Blesch, et al. (1999) J Neurosci. 19:3556-66). Typically infusion pumps or gene therapy techniques are used to deliver growth factors to injured neurons. In general, trophic factors do not stimulate long distance regeneration, but stimulate more of a local sprouting response (Schnell, et al. (1994) Nature. 367:170-173, Mansour-Robaey, et al. (1994) Proc. Natl. Acad. Sci. 91:1632-1636).

A more recent advance is the demonstration that increasing the intrinsic growth capacity of neurons is sufficient to allow axon regeneration in the CNS, and that neurons primed for regeneration with neurotrophins, a conditioning lesion, or treatment with Rho antagonists have a better chance to grow on inhibitory substrates (Neumann (1999) Neuron. 23:83-91, Cai, et al. (1999) Neuron. 22:89-101, Lehmann, et al. (1999) J. Neurosci. 19:7537-7547). Targeting intracellular signalling mechanisms is likely to be the most efficient way to promote axon regeneration, and it has been found that Rho antagonists are able to stimulate regeneration in the optic nerve of adult rats (Lehmann et al (1999) IBID). However, preliminary experiments to apply Rho antagonists to the injured spinal cord were not successful. It is believed that the infused protein was not sufficiently retained at the injury site, either by syringe application or the use of Gelfoam. This suggested that the delivery of compounds that act with low affinity (compared to high affinity neurotrophins) posed unique problems in delivery. As shall be discussed in greater detail below the present invention relates to a tissue-adhesive delivery system whereby the Rho antagonist is added to the adhesive solution before application of the solution with a syringe, and polymerization of the adhesive within the lesion cavity in the CNS.

While neurons in the peripheral nervous system regenerate naturally, there are many techniques used to enhance and help the repair process. Most of these techniques are not aimed at stimulating the rate of axonal regeneration, but in helping to guide axons back towards their target regions. For example, severed nerve are sewn or glued together with a fibrin glue enhance the repair process. While the following discussion will generally relate or be directed at repair in the CNS, the techniques described herein may be extended to use in PNS repair. Treatment with Rho antagonists in the adhesive delivery system could be used to enhance the rate of axon growth in the PNS. This is first use of Rho antagonists in the PNS.

Growth inhibitory proteins cause growth cone collapse (Li, et al. (1996) J. Neurosci. Res. 46:404-414, Fan, et al. (1993) J. Cell Biol. 121:867-878) and it has become clear that GTPases of the Rho family that comprise Rho, Rac and Cdc42 are intracellular regulators of growth cone collapse (Lehmann, et al. (1999) J. Neurosci. 19:7537-7547, Tigyi, et al. (1996) Journal of Neurochemistry. 66:537-548, Kuhn, et al. (1999) J. Neurosci. 19:1965-1975, Jin and Strittmatter (1997) J. Neurosci. 17:6256-6263). These small GTPases exist in inactive (GDP) and active (GTP) forms, and the cycling between active GTP-bound and inactive GDP-bound states is tightly regulated. The guanine nucleotide exchange factors (GEFs) accelerate the release of GDP, thereby facilitating GTP binding. The GTPase activating proteins (GAPs) catalyze GTP hydrolysis and conversion of the inactive form. The GDP dissociation inhibitors (GDIs) act to maintain Rho in a GDP-bound form. GEFs for Rho all have a domain homologous with the Db1 oncoprotein, and more than 20 such proteins have been identified, including Tiam-1 which is highly expressed in brain (Zheng and Li (1999) J. Biol. Chem. 272:4671-4679, van Leeuwen, et al. (1997) J. Cell Biol. 139:797-807). Once in the active form, Rho GTPases typically stimulate ser/thr kinases, such as ROK (Rho kinase), PAK (p21-activated kinase) and downstream effectors that act on the cytoskeleton.

The Rho family members that regulate the cytoskeleton and motility include Rho, Rac and Cdc42 (Nobes and Hall (1995) Cell 1995 81:53-62). Rho is an important link between signaling through integrins and signaling cascades of trophic factors (Laudanna, et al. (1996) Science. 271:981-983, Hannigan, et al. (1996) Nature. 379:91-96, Kuhn, et al. (1998)J. Neurobiol. 37:524-540). Cdc42 is important for the regulation of filopodia (Nobes and Hall (1995) Cell 1995.81:53-62). Both Rac and Rho regulate growth cone motility and axon growth. In non-neuronal cells a hierarchy of signaling between Rho, Rac and Cdc42 exists (Hall (1996) Ann. Rev. Cell Biol. 10:31-54). In neurons Rac and Rho may have opposite effects (van Leeuwen, et al. (1997) J. Cell Biol. 139:797-807, Kozma, et al. (1997) Molec. Cell. Biol. 17:1201-1211). Activation of Rac stimulates outgrowth of neurites from NIE-115 neuroblastoma neurons whereas activation of Rho causes neurite retraction (van Leeuwen, et al. (1997) J. Cell Biol. 139:797-807, Albertinazzi, et al. (1998) J. Cell Biol. 142:815-825). In PC12 cells, dominant negative Rac disrupts neurite outgrowth in response to NGF (Hutchens, et al. (1997) Molec. Biol. Cell. 8:481-500, Daniels, et al. (1998) EMBO Journal. 17:754-764) whereas treatment of PC12 cells with lysophosphatidic acid (LPA), a mitogenic phospholipid that activates Rho, causes neurite retraction (Tigyi, et al. (1996) Journal of Neurochemistry. 66:537-548).

The p21-activated kinase(PAK) is activated by Rac, and PAK can also induce PC12 cell neurite outgrowth (Daniels, et al. (1998) EMBO Journal. 17:754-764). It has been shown that inactivation of Rho is sufficient to promote PC12 cell neurite outgrowth on growth inhibitory substrates (Lehmann, et al. (1999)J. Neurosci. 19:7537-7547). A recent study of activating and null mutations of Rho expressed in PC12 cells suggests that the differentiation state is an important parameter for the effect of Rho on neurite outgrowth, and that priming PC12 cells with NGF can alter the responsiveness to activating and null mutations (Sebok, et al. (1999) J. Neurochem. 73:949-960). This result is in agreement with the finding that priming neurons increases intracellular cAMP (Cai, et al. (1999) Neuron. 22:89-101), which can in turn influence the activation of Rho (Lang, et al. (1996) EMBO J. 15:510-519, Dong, et al. (1998) J. Biol. Chem. 273:22554-22562).

In primary neurons Rac and Rho regulate both dendrite and axon growth and cone morphology and collapse. By immunocytochemistry it has been demonstrated that Rho is concentrated in growth cones, and some colocalizes at sites of point contact (Renaudin, et al. (1998) J. Neurosci. Res. 55:458-471). Experiments with activating and dominant negative mutations have demonstrated that activation of Rac is important in maintaining a spread morphology after challenge with growth cone collapsing factors (Kuhn, et al. (1999) J. Neurosci. 19:1965-1975, Jin and Strittmatter (1997) J. Neurosci. 17:6256-6263). The activation of Rho induces growth cone collapse, and collapse can be prevented by treatment with *Clostridium botulinum* C3 exotransferase (hereinafter simply referred to as C3) (Tigyi, et al. (1996) Journal of Neurochemistry. 66:537-548, Jin and Strittmatter (1997) J. Neurosci. 17:6256-6263). C3 inactivates Rho by ADP-ribosylation and is fairly non-toxic to cells (Dillon and Feig (1995) Methods in Enzymology: Small GTPases and their regulators Part. B. 256:174-184).

An important downstream target of activated Rho is p160ROK, a Rho kinase (Kimura and Schubert (1992) Journal of Cell Biology. 116:777-783, Keino-Masu, et al. (1996) Cell. 87:175-185, Matsui, et al. (1996) EMBO J. 15:2208-2216, Matsui et al. (1998) J. Cell Biol. 140:647-657, Ishizaki (1997) FEBS Lett. 404:118-124). Among other effects, ROK phosphorylates myosin phosphatase to regulate actin-myosin based motility (Matsui et al. (1996) EMBO J. 15:2208-2216) and regulates proteins of the ezrin family (Vaheri, et al. (1997) Curr. Opin. Cell Biol. 9:659-666), which are concentrated in neuronal growth cones (Goslin, et al. (1989) J. Cell Biol. 109:1621-1631). Activation of ROK also induces growth cone collapse, which can be prevented by the addition of the ROK inhibitor Y-27632 (Hirose, et al. (1998) J. Cell Biol. 141:1625-1636).

The above studies showed that Rho antagonists can stimulate regeneration in the CNS. It has been demonstrated that Rho kinase is an important downstream target of Rho signaling (Matsui, et al. (1996) EMBO J. 15:2208-2216, Bito (2000) Neuron. 26:431-441). Among other effects, inactivation of Rho kinase stimulates neurite outgrowth in tissue culture (Bito (2000) Neuron. 26:431-441) as does inactivation of Rho (Lehmann, et al. (1999) J. Neurosci. 19:7537-7547). Therefore, inactivation of Rho kinase should induce the same biological effects in vivo as inactivation of Rho.

The Rho kinase inhibitory Y-27632 compound is a trans-4-amino(alkyl)-1-pyridylcarbamoylcyclohexane compound; this compound is for example described in U.S. Pat. No. 4,997,834 the entire contents of which are incorporated herein by reference; this patent refers for example to compounds which may be selected from the group consisting of trans-4-aminomethyl-1-(4-pyridylcarbomoyl)cyclohexane, trans-4-aminomethyl-trans-1-methyl-1-(4-pyridylcarbamoyl)cyclohexane, trans-4-aminomethyl-cis-2-methyl-1-(4-pyridylcarbamoyl)cyclohexane, trans-4-aminomethyl-1-(2-pyridylcarbamoyl)cyclohexane, trans-4-aminomethyl-1-(3-pyridylcarbamoyl)cyclohexane, trans-4-aminomethyl-1[(3-hydroxy-2-pyridylcarbamoyl)]cyclohexane, trans-4-aminomethyl-1-(3-methyl-4pyridylcarbamoyl)cyclohexane, 4-(trans-4-aminomethylcyclohexylcarboxamido)-2,6-dimethyl-pyridine-N-oxide, trans-4-aminomethyl-1-(2-methyl-4-pyridylcarbamoyl)cyclohexane, trans-4-(2-aminoethyl)-1-(4-pyridylcarbamoyl)cyclohexane, trans-4-(1-amino-1-methylethyl)-1-(4-pyridylcarbamoyl)cyclohexane, trans-4-(1-aminopropyl)-1-(4-pyridylcarbamoyl)cyclohexane, and pharmaceutically acceptable acid addition salts thereof.

Please also see also Ishizali et al. 2000. Molecular Pharmacology 57:976-983 3 which refers to Y-27632 in the dihydrochloride form as well as to a related compound Y-30141, namely (R)-trans-4-(1-aminoethyl)-N-(1H-pyrrolo[2,3]pyridin-4-yl) cyclohexanecarboamide dihydrochloride. A patent application A Medicines comprising Rho kinase inhibitor has been submitted-(EPO 956 865 A1). This inhibitor has not been tested for efficacy in CNS injury, nor has the company who patented this compound discovered how it might to applied to a region of CNS injury in a kit form. Such a kit is provided in our invention. Please see also European Patent application no. 97934756.4; PCT/JP97/02793; International publication # WO 98/06433 (19.02.1998/07).

The compound Y-27632 has the following structure

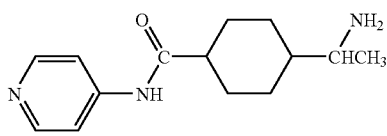

The above structure is used herein in a pharmaceutically acceptable salt form (e.g. dihydrochloride salt).

The above mentioned related compound Y-30141 which may be exploited in accordance with the present invention has the following structure:

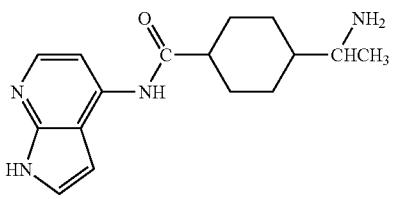

Again the above structure may also be used herein in a pharmaceutically acceptable salt form (e.g. dihydrochloride salt).

The compound (R)-(+)-trans-N-(4-pyridyl)-4-(1-aminoethyl)-cyclohexanecarboamide (Y-27632) inhibits Rho kinase at sub-micromolar concentrations (Uehata, et al. (1997) Nature. 389:990-994). Y-27632, made by a Yoshitoma, affects calcium sensitization of smooth muscles to affect hypertension. It was reported that the cellular target of Y-27632 is Rho-associated protein kinase, p160ROCK (Uehata, et al. (1997) Nature. 389:990-994, Somlyo (1997) Nature. 389:908-911).

Different methods have been used for local delivery of drugs in the CNS, however none of these methods have been developed as a kit with biological component that have proven effective in the promotion of the regeneration of injured axons. IN-1 is an antibody that promotes regeneration in the CNS. One method of delivery is the implantation of cells that secrete the active antibody (Schnell et al (1994) Nature 367:170). The use of fibrin adhesive for the delivery of IN-1 antibody was not found to be effective (Guest (1997) J. Neurosci. Res. 50:888-905). Another method is the use of pumps to infuse and deliver continuously over time compounds that stimulate regeneration. (Ramer, et al. 2000, Nature. 403:312-316, Verge, et al. 1995. Journal of Neuroscience. 15:2081-2096).

Fibrin adhesives per se have been used in studies of CNS regeneration. It has been used in replacement of sutures to graft peripheral nerves into the damaged CNS (Cheng, et al. (1996) Science. 273:510-513). A fibrin glue has also been used for the delivery of fibroplast growth factor (FGF) to damaged corticospinal neurons (Guest (1997) J. Neurosci. Res. 50:888-905). The use of fibrin glue plus FGF did not promote long distance regeneration.

Collagen per se has been tested for its ability to promote regeneration after injury (Joosten (1995) J. Neurosci. Res. 41:481-490). Collagen has also been used for the delivery of neurotrophins to injured corticospinal axons (Houweling (1998) Expt. Neurol. 153:49-59). Neither of the conditions was able to support long distance regeneration. In tissue culture, collagen gels can maintain gradients of small molecules important in axon guidance (Kennedy, et al. (1994) Cell. 78:425-435). Moreover, it had been reported that collagen gels by themselves could foster some axon regeneration after spinal cord injury (Joosten (1995) J. Neurosci. Res. 41:481-490).

Many different protein-based tissue adhesives exist Examples include collagen gels, fibrin tissue adhesives, matrigel, laminin networks, and adhesives based on a composition of basement membrane proteins that contain collagen: Perhaps the most popular are the fibrin adhesives.

Fibrin sealant has three basic components: fibrinogen concentrate, calcium chloride and thrombin. Other components can be added to affect the properties of the gel formation. Added components are used to modulate time it takes for the fibrin gel to form from the soluble components, the size of the protein network that is formed, the strength of the gel, and protease inhibitors slow down the removal of the gel after it is place in the body. Several different commercial preparations are available as kits. These include Tissucol/Tisseel, (Immuno AG, Vienna, now marketed by Baxter), Beriplast P, (Hoechst, West Germany), and Hemaseel (Hemacure Inc. Kirkland, Quebec).

To make a fibrin gel soluble thrombin and fibrinogen are mixed in the presence of calcium chloride. When the components mix, a fibrin adhesive gels is formed because the fibrinogen molecule is cleaved by thrombin to form fibrin monomers. The fibrin monomers spontaneously will polymerize to form a three-dimensional network of fibrin, a reaction that mimics the final common pathway of the clotting cascade, i.e. the conversion of fibrinogen to fibrin sealant. The key to the preparation of commercial preparations is to keep the fibrinogen and thrombin components separate until use, so that the polymerization can be controlled with the desired timing before or after application to the body.

Today such use of fibrin as a biological adhesive has been widely accepted and found application in many fields of surgery. HEMASEELJ or Tisseel VH are used as an adjunct to hemostasis in surgeries involving cardiopulmonary bypass and treatment of splenic injuries due to blunt or penetrating trauma to the abdomen, when control of bleeding by conventional surgical techniques, including suture, ligature and cautery is ineffective or impractical. The action of these fibrin gels is also used to stop bleeding in surgical procedures involving cardiopulmonary bypass and repair of the spleen. Tisseel VH has also been shown to be an effective sealant as an adjunct in the closure of colostomies.

Collagen gels have been used in tissue culture studies to main gradients of diffusible molecules. The use of collagen gels has permitted the identification and testing of neuronal guidance factors such as netrins (Kennedy, et al. (1994) Cell. 78:425-435). When collagen polymerized it forms a dense protein network. Therefore, like fibrin, it has the potential to act as a tissue adhesive. Moreover, collagen is easy to purify in large quantities.

There are many different types of collagens, and it is a major component of basement membranes in many different body tissues. The form of collagen often used for experimental studies in rodents is type IV collagen because it is easily purified from rat tails.

Not only is collagen a component of the basement membrane in the peripheral nervous system, but it is known that neurons express receptors for collagen. Receptors for collagens are receptors of the integrin class of proteins. One important collagen receptor expressed by neurons is the alpha1 beta1 receptor (McKerracher, et al. 1996. Molec. Neurobiol. 12:95-116); this receptor is involved in the promotion of neurite outgrowth. When PC12 cells, a neuronal cell line, are plated on collagen substrates in tissue culture, collagen helps promote neurite growth in an integrin-dependent fashion. The addition of anti-integrin antibodies block neurite outgrowth. Therefore, the ability of collagen, by itself, has been tested for its ability to promote axon regeneration after spinal cord injury. It was reported that collagen gels by themselves could foster some axon regeneration after spinal cord injury (Joosten (1995) J. Neurosci. Res. 41:481-490). However, the observed growth was more of a sprouting response with out any long distance regeneration past the glial scar and site of the lesion. In addition, collagen has been tested for its ability to promote regeneration after injury in conjunction with the delivery of neurotrophins to injured corticospinal axons (Houweling (1998) Expt. Neurol. 153:49-59). This treatment was not able to support long distance regeneration, although the treated animals had a better sprouting response than the controls.

It would be advantageous to have a means for the direct delivery to and maintenance at a lesion site of an agent able to facilitate axon growth at the lesion site.

SUMMARY OF THE INVENTION

As discussed herein in accordance with the present invention a therapeutically active agent for facilitating axon growth may be delivered (in a flowable matrix forming substance) to a (nerve) lesion site, for example, by injection using known syringe type glue or sealant devices modified as necessary or desired (e.g. by addition of a further substance container); examples of known delivery devices, systems, mechanisms, matrix forming compositions, and the like are shown for example in U.S. Pat. No. 5,989,215, U.S. Pat. No. 4,978,336, U.S. Pat. No. 4,631,055, U.S. Pat. No. 4,359,049, U.S. Pat. No. 4,974,368, U.S. Pat. No. 6,121,422, U.S. Pat. No. 6,047,861, U.S. Pat. No. 6,036,955, U.S. Pat. No. 5,945,115, U.S. Pat. No. 5,900,408, U.S. Pat. No. 6,124,273, U.S. Pat. No. 5,922,356, and in particular U.S. Pat. No. 6,117,425; the entire contents of each of these patents is incorporated herein by reference.

A sufficient amount of a therapeutically active agent for facilitating axon growth may be dispersed in a stable flowable (known) type of (proteinaceous) matrix forming material. Once delivered to the desired lesion site the resulting in situ or in vivo matrix (e.g. gel or crosslinked substances) inhibits the migration or diffusion of the agent from the site of injection, so as to maintain the primary effect of the agent in the region of injection, i.e. in the area of the lesion. In any event the active agent is to be present in an amount effective to facilitate axon growth.

A substantially uniform dispersion of the active agent may be initially be formed so as to provide a concentrated amount of active agent in a physiologically acceptable matrix forming material. The matrix forming material may be comprised of any (known) individual or combination of peptides, proteins etc. which provides for stable placement, or combinations thereof. Of particular interest is a collagen material, a fibrinogen material, or derivatives thereof; other high molecular weight physiologically acceptable biodegradable protein matrix forming materials may if desired be used. The active agent may, for example, be incorporated in a sufficient concentration so as to provide the desired or effect the desired sustained release.

Typically when estimating doses in different animal species, the same weight ratio is used. It is for example possible to apply 40 ug protein per 20 gm mouse. Therefore, we anticipate that the ideal dose should be approximately 3 gm per 60 kg person. We expect that the dose necessary will depend on the size of the lesion and the time of application (acute or chronic) spinal cord injury. In cases of chronic injury, there is often a necrotic center in the spinal cord, and higher doses may be required.

The matrix forming material may be a one-component adhesive or sealant type material (e.g. collagen material); alternatively it may be a multi-component adhesive or sealant (e.g. a fibrinogen based material). The matrix may be a human protein matrix or if necessary or desired a non-human protein matrix; preferably a human protein matrix.

The (proteinaceous) matrix forming material is flowable for injection, but once in vivo it provides for stable placement, of the active agent in the lesion area; i.e. after injection, the active agent is released into the immediate environment the matrix providing a medium for prolonged contact between a lesion site and the active agent (i.e. axon growth facilitator or stimulant).

The matrix forming material(s) is (are) of course to be chosen on the basis that the materials and resultant formed matrix will be capable on the one hand of holding the active agent for release in situ and on the other without preventing the therapeutic effect thereof, i.e. the matrix is to be therapeutically acceptable. The choice of active agent may be determined empirically through appropriate or suitable assays keeping in mind that the matrix etc. are to be therapeutically acceptable.

The present invention in an aspect relates to a biocompatible, (supplemented tissue sealant or adhesive) composition comprising: (i) at least one supplement selected from the group consisting of therapeutically active agents for facilitating axon growth; and (ii) a flowable carrier component capable of forming a pharmaceutically or therapeutically acceptable matrix (in vivo)—i.e. a nerve lesion site; wherein said supplement is releasable from said matrix into the adjacent external environment (e.g. for a sustained period of time).

The present invention in another aspect relates a method for the preparation of a flowable biocompatible composition comprising admixing (i) at least one supplement selected from the group consisting of therapeutically active agents for facilitating axon growth and (ii) a flowable carrier component capable of forming a therapeutically acceptable matrix in vivo at a nerve lesion site; wherein said supplement is releasable from said matrix into the adjacent external environment.

By way of example only in accordance with the present invention a method of applying an supplemented solution of polymerizable fibrin to a desired lesion site, may comprise a) affixing a cartridge containing immobilized thrombin to a syringe containing a solution of fibrinogen, b) contacting the solution of fibrinogen with immobilized thrombin under conditions resulting in an activated solution of polymerizable fibrin by passing the solution of fibrinogen through the cartridge containing immobilized thrombin, c) adding to the fibrinogen solution or to the activated solution a supplement (i) at least one supplement selected from the group consisting of therapeutically active agents for facilitating axon growth; and c) delivering the supplemented activated solution of polymerizable fibrin to the desired lesion site (e.g. a central nervous system (CNS) lesion site or a peripheral nervous system (PNS) lesion site) under conditions which result in polymerized fibrin at the lesion site having dispersed therein the supplement wherein said supplement is released from said fibrin matrix into the adjacent external environment.

In accordance with another aspect the present invention relates to a kit comprising, in suitable container means (e.g. separate means): (a) a first pharmaceutical composition or substance comprising a biological agent capable of facilitating axon growth; and (b) a second pharmaceutically or therapeutically acceptable component comprising a single flowable carrier component or two or more separate components capable once intermingled of forming a flowable carrier component, said flowable carrier components each being capable of forming a pharmaceutically or therapeutically acceptable matrix (e.g. proteinaceous matrix, i.e. a proteinaceous glue, proteinaceous sealant, proteinaceous gel, etc.; e.g. a human derived proteinaceous matrix) in vivo at a (nerve) lesion site.

In particular the present invention provides a (axon growth stimulation) kit comprising a) a first container means (e.g. one or more separate containers) for containing a flowable carrier component(s) or two or more separate components capable once intermingled of forming a flowable carrier component, said flowable carrier components each being capable of forming a pharmaceutically or therapeutically acceptable matrix (e.g. proteinaceous matrix, i.e. a proteinaceous glue, proteinaceous sealant, proteinaceous gel, etc.; i.e. a human derived proteinaceous matrix) in vivo at a (nerve) lesion site (e.g. a central nervous system (CNS) lesion site or a peripheral nervous system (PNS) lesion site) and b) a second container means for containing a therapeutically active agent for facilitating axon growth at the lesion site wherein said therapeutically active agent supplement is releasable from said in vivo matrix into the adjacent external environment (e.g. for a sustained period of time). Alternatively, if desired or as necessary, the first and second container means may be the same, (e.g. a container may hold collagen and C3). The kit may if desired or necessary additionally comprise means for dispersing (i.e. co-mingle, blend, etc.) the therapeutically active agent in said flowable carrier component so as to form a flowable axon growth stimulation composition as well as means for delivering the flowable axon growth stimulation composition to the lesion site (e.g. syringe needle). The pharmaceutically acceptable matrix may as discussed herein be a collagen matrix or a fibrin matrix.

In accordance with the present invention the therapeutically active agent for facilitating axon growth may for example be a Rho antagonist which may be identified by an assay method comprising the following steps:

a) culturing neurons on inhibitory substrate or a substrate that incorporates a growth-inhibitory protein.
b) Exposing the cultured neuron of step a) to a candidate Rho antagonist in an amount and for a period sufficient to permit growth of neurites, and determining if the candidate has elicited neurite growth from the cultured neurons of step a), the appearance of neurites being suggestive or indicative of a Rho antagonist.

A compound can be confirmed as a Rho antagonist in one of the following ways:

a) Cells are cultured on a growth inhibitory substrate as above, and exposed to the candidate Rho antagonist;
b) Cells of step a) are homogenized and a pull-down assay is performed. This assay is based on the capability of GST-Rhotektin to bind to GTP-bound Rho. Recombinant GST-Rhotektin or GST rhotektin binding domain (GST-RBD) is added to the cell homogenate made from cells cultured as in a). It has been found that inhibitory substrates activate Rho, and that this activated Rho is pulled down by(GST-RBD). Rho antagonists will block activation of Rho, and therefore, an effective Rho antagonist will block the detection of Rho when cell are cultured as described by a) above;
c) An alternate method for this pull-down assay would be to use the GTPase activating protein, Rho-GAP as bait in the assay to pull down activated Rho, as described (Diekmann and Hall, 1995. In Methods in Enzymology Vol. 256 part B 207-215).

Another method to confirm that a compound is a Rho antagonist is as follows: When added to living cells antagonists that inactivate Rho by ADP-ribosylation of the effector domain can be identified by detecting a molecular weight shift in Rho (Lehmann et al, 1999 IBID). The molecular weight shift can be detected after treatment of cells with Rho antagonist by homogenizing the cells, separating the proteins in the cellular homogenate by SDS polyacrylamide gel electrophoresis. The proteins are transferred to nitrocellulose paper, then Rho is detected with Rho-specific antibodies by a Western blotting technique.

Another method to confirm that compound is a Rho-kinase antagonist is as follows:

a) Recombinant Rho kinase tagged with myc epitope tag, or a GST tag is expressed in HeLa cells or another suitable cell type by transfection.
b) The kinase is purified from cell homogenates by immunoprecipation using antibodies directed against the myc tag or the GST tag.
c) The recovered immunoprecipitates from b) are incubated with [32P] ATP and histone type 2 as a substrate in the presence or absence of the Rho kinase. In the absence of Rho kinase activity the Rho kinase antigens is able to block the phosphorylation activity of Rho kinase (i.e. phosphorylation of hislore), and as such identified the compound as a Rho kinase antagonist.

The present invention is in particular,concerned with a delivery system and kit to apply for example, known C3, chimeric C3, or Y-27632 type compounds (e.g. Y-27632, Y-30141 and the like) or a Rho kinase inhibitor to injured regions of the CNS that include injured spinal cord or brain, and regions of the CNS injured by stroke. The nature of C3 is discussed herein; Y-27632 is for example mentioned above.

In the context of the present invention, the ability of C3 to stimulate (axon) regeneration in vivo was examined. Thus adult rat optic nerves were crushed an C3 applied at the same time, directly at the lesion site (Lehmann, et al. (1999) J. Neurosci. 19:7537-7547). It was found that large numbers of axons traversed the lesion to grow in the distal optic nerve. In particular there was for example examined the delivery of C3 to optic nerve through the use of gelfoam an Elvax, a slow release matrix (Lehmann, et al. (1999) J. Neurosci. 19:7537-7547).

It has also been found that the combination of collagen gels and C3 was able to allow axons to into the site of the glial scar. Based on experiments with fibrin glue (see below), it is believed that delivery of C3 in collagen may be improved by the addition of protease inhibitors to prevent lysis of the gel and C3.

However, the present invention as mentioned above is directed to the delivery system of a therapeutically active agent (such as for example a Rho antagonist—C3, Y-27632, etc.) in a protein matrix that holds the active agent (e.g. Rho antagonist) at the site of application. This delivery system retains the active agent (e.g. Rho antagonist) at the site of CNS injury, allows large doses to be given at the site of injury, and prevents large amounts of the active agent (e.g. Rho antagonist) from leaking into the systemic circulation. The protein matrix can either be based on the fibrin, a protein of the coagulation pathway, or it can be based on collagen, a protein of the extracellular matrix. Both proteins when applied under specific conditions form protein networks when polymerized. These proteins can be applied in soluble form with the additional components necessary for polymerization, together with the Rho antagonist. When the components are mixed immediately before use, polymerization occurs after application to the body site, in our case after application to the CNS.

The present invention as mentioned above in particular relates to a kit suitable for use in the above-described method of delivering fibrin sealant components to a wound site. The kit comprises individually packaged component solutions provided in separate bottles to prevent mixing before use, and an applicator designed so as to permit mixing of the fibrinogen/Factor XIII and thrombin with C3 at the body site. The kit provides pre-measured amounts of the fibrinogen and factor XIII in one bottle, the thrombin in another bottle, a C3 solution in another bottle. The contents of the bottles would be mixed in a prescribed order, as detailed in the example below. The kit can also include one or more other storage containers which are any necessary reagents including solvents, buffers, calcium chloride, protease inhibitors etc. The kit could be sold as lyophilized or frozen components to preserve the activity of C3 or other Rho antagonist added to the kit.

Rho antagonist delivery system may be used in conjunction cell transplantation. Many different cell transplants have been extensively tested for their potential to promote regeneration and repair. These include, but are not restricted to, Schwann cells (Xu, et al. (1996) Exp. Neurol. 134:261-272, Guest (1997) Exp. Neurol. 148:502-522, Tuszynski, et al. (1998) Cell Transplant. 7:187-96), fibroblasts modified to express trophic factors (Liu, et al. (1999) J Neurosci. 19:4370-87, Blesch, et al. (1999) J Neurosci. 19:3556-66, Tuszynski, et al. (1994) Exp Neurol. 126:1-14, Nakahara, et al. (1996) Cell Transplant. 5:191-204), fetal spinal cord transplants (Diener and Bregman (1998) J. Neurosci. 18:779-793, Bregman (1993) Exp. Neurol. 123:2-16), macrophages (Lazarov-Spiegler, et al. (1996) FASEB. J. 110:1296-1302), embryonic stem cells (McDonald, et al. (1999) Nat Med. 5:1410-2), and olfactory ensheathing glia (Li, et al. (1997) Science. 277: 2000-2002, Ramon-Cueto, et al. (1998) J Neurosci. 18:3803-15, Ramon-Cueto, et al. (2000) Neuron. 25:425-35).

Brief description of the figures which illustrate example embodiments of the present invention:

FIG. 1A is a schematic diagram of adhesive delivery system of C3 applied to an injured spinal cord wherein a tissue adhesive plus Rho antagonist (i.e. C3) is injected into the site of injury;

FIG. 1B is a schematic diagram of adhesive delivery system of C3 applied to an injured spinal cord wherein the injection is shown as resulting in axon regeneration through the supplemented adhesion matrix and into the distal spinal cord;

FIG. 2 Schematically illustrates the model used to show efficacy in vivo. A dorsal hemisection was made in adult mice. Three to four weeks later the anterograde tracer WGA-HRP was injected into the cortex to label the neurons of the corticospinal tract. Two days later the spinal cord was removed and HRP enzymatic activity revealed to detect the CST axons. The corticospinal tract of adult mice was lesion at the T6 level, and the fibrin glue/C3 was added at the time of lesion with a syringe. The expression CST refers to cortical spinal tract.

Figure 3:
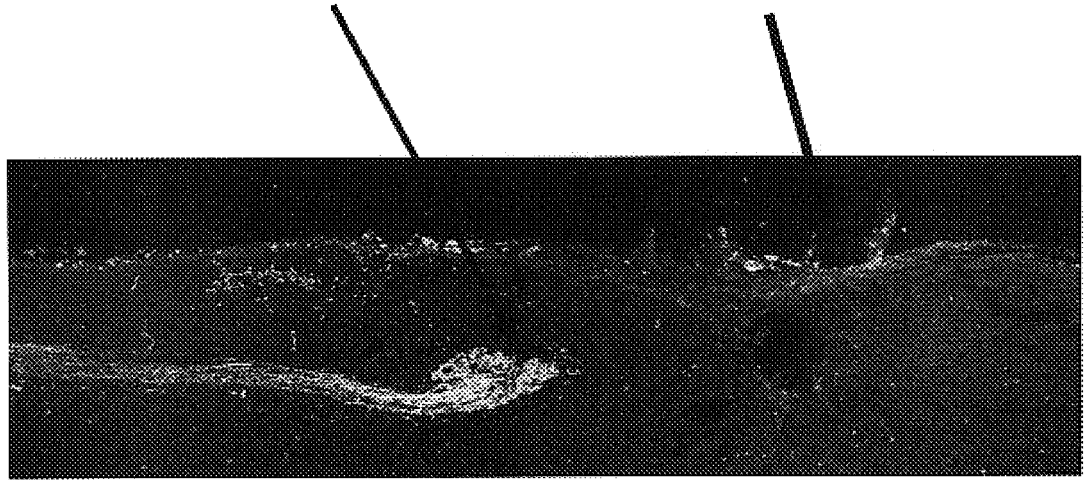

FIG. 3 Illustrates a longitudinal section of an untreated adult mouse spinal cord 3 weeks after lesion of the corticospinal tract viewed by darkfield microscopy. The fibres were anterogradely labeled from the motor cortex and appear fluorescent. The fibres retract back from the site of the lesion and do not regenerate with treatment.

Figure 4A:
Figure 4B:
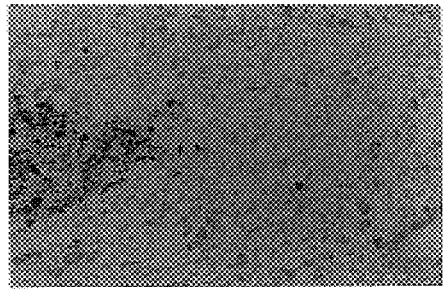
Figure 4C:
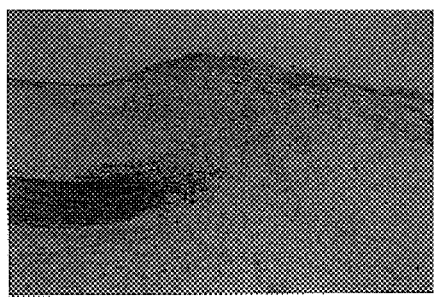
Figure 4D:
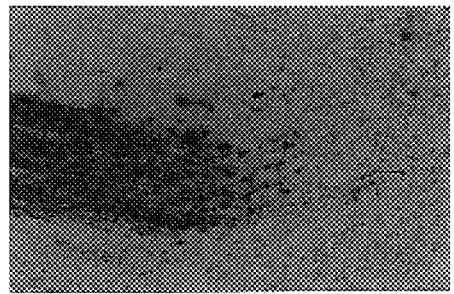
Figure 5A:
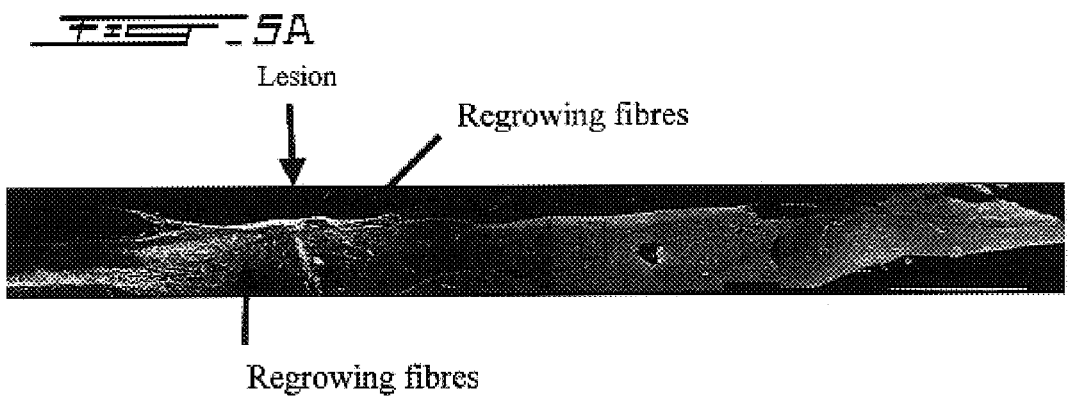
Figures 5B, 5C:
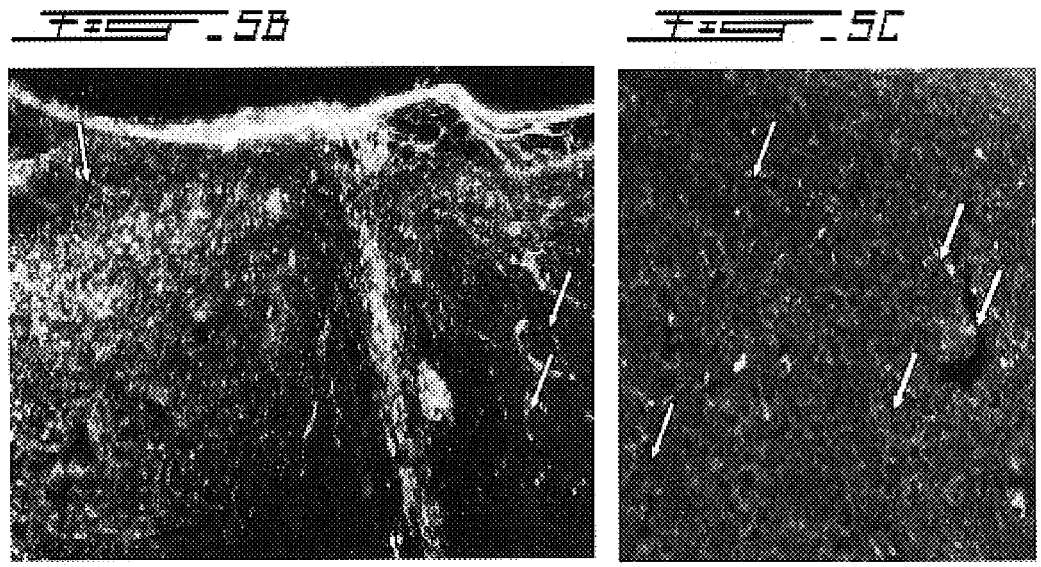
Figure 6A:
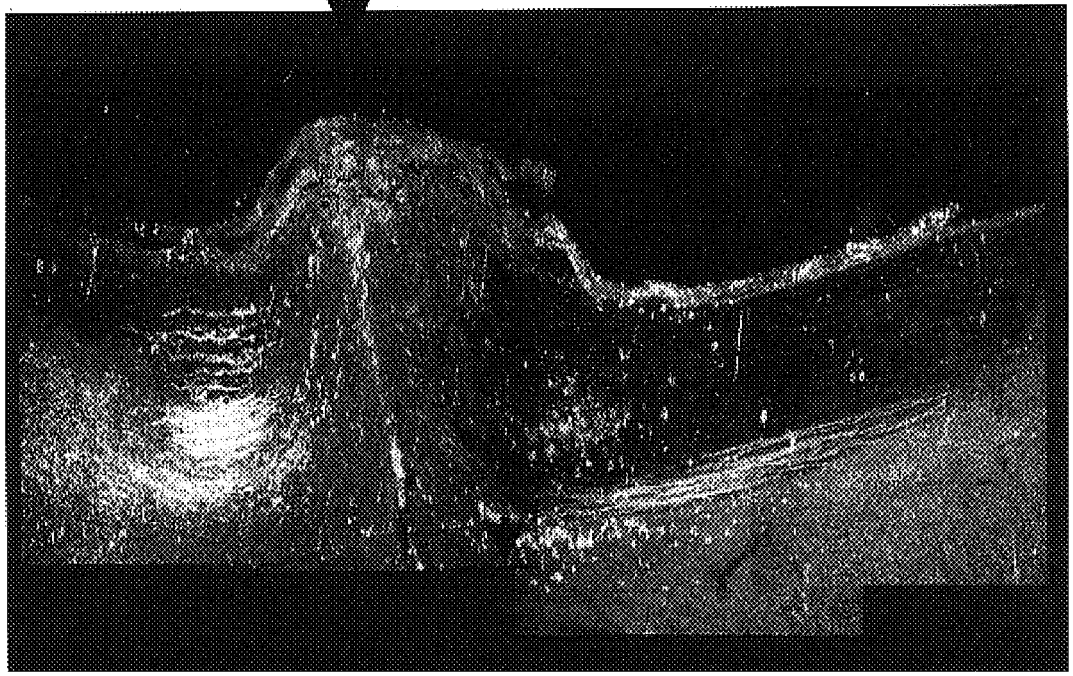
Figure 6B:
Figure 7A:
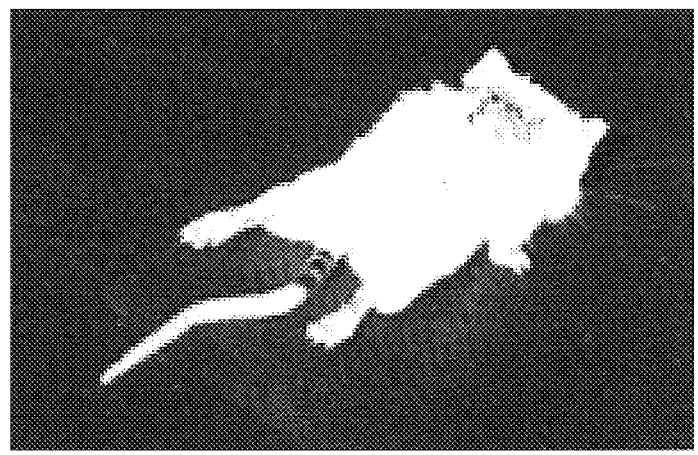
Figure 7B:

FIG. 4A Illustrates a low magnification view of a control animal treated with collagen gel without C3; axons retract from the site of lesion;

FIG. 4B Illustrates a higher magnification view of a spinal cord treated with collagen gel without C3; axons do not regenerate;

FIG. 4C Illustrates a low magnification view of labelled corticospinal axons near the lesion site after treatment with collagen gel with C3 as a Rho antagonist; axons do not retract back from the lesion site; thy extend into the region of increased cellularity which is the scar;

FIG. 4D Illustrates a higher magnification view of FIG. 4C showing that treatment with Rho antagonist is a collagen gel allows some axons to sprout into the lesion site;

FIG. 5A Illustrates a low magnification view of a spinal cord following treatment with fibrin adhesive with C3 as a Rho antagonist; the section is viewed by darkfield to show the anterogradely-labeled fibres that appear white;

FIG. 5B Illustrates a high magnification view of the lesion site shown in FIG. 5A showing that axons grow through the scar region; the scar appears as the vertical line;

FIG. 5C Illustrates a high magnification view approximately 7 mm distal o the lsion set of the spinal cord shown in FIGS. 5A and 5B; the regenerating fibres (arrows) grow long distances;

FIG. 6A Illustrates a darkfield microscopy of a spinal cord section after treatment with Rho antagonist C3 in a fibrin adhesive showing long distance regeneration; axons sprout into the white matter and cross the lesion site;

FIG. 6B Illustrates a section of the same spinal cord shown in FIG. 6A to show axons that have regenerated a distance of 10 mm from the lesion site;

FIG. 7A Illustrates an untreated mouse two days after spinal cord injury; the control mouse is mobile but uses its front paws to drag itself forward and it shows some movement of hindlimb joints;

FIG. 7B Illustrates an animal 2 days after spinal cord injury and treatment with C3/matrix; the animal is able to walk with weight support two days after treatment;.

Figure 7C:
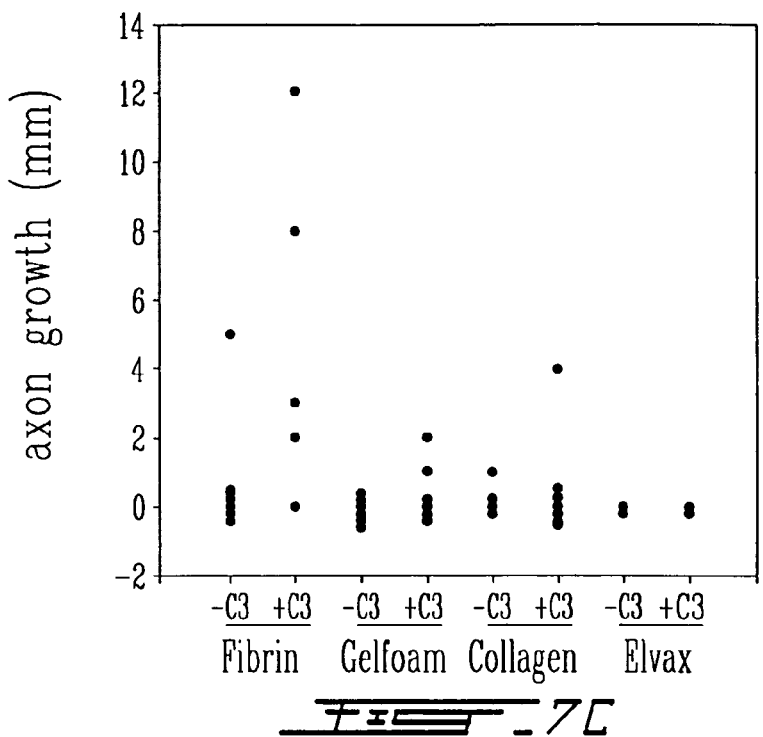
Figure 8:
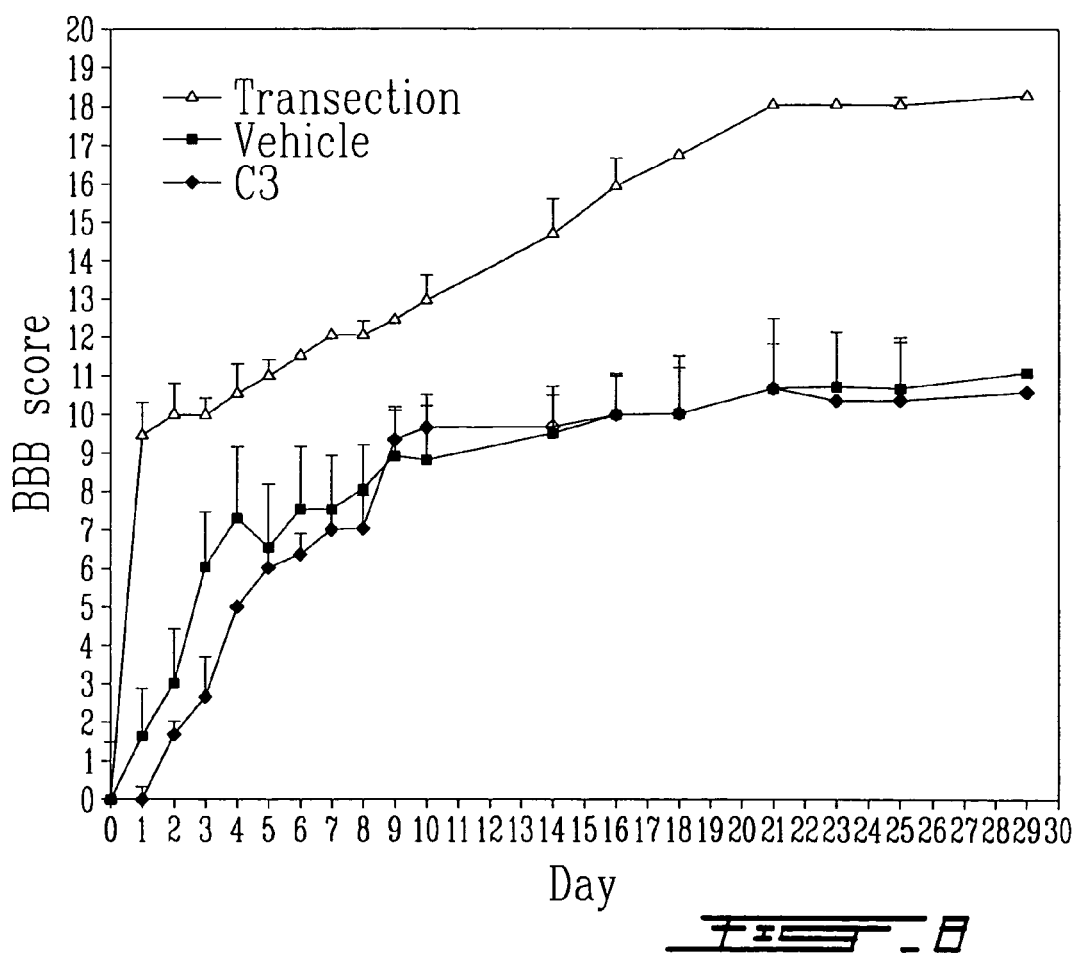
Figure 9:
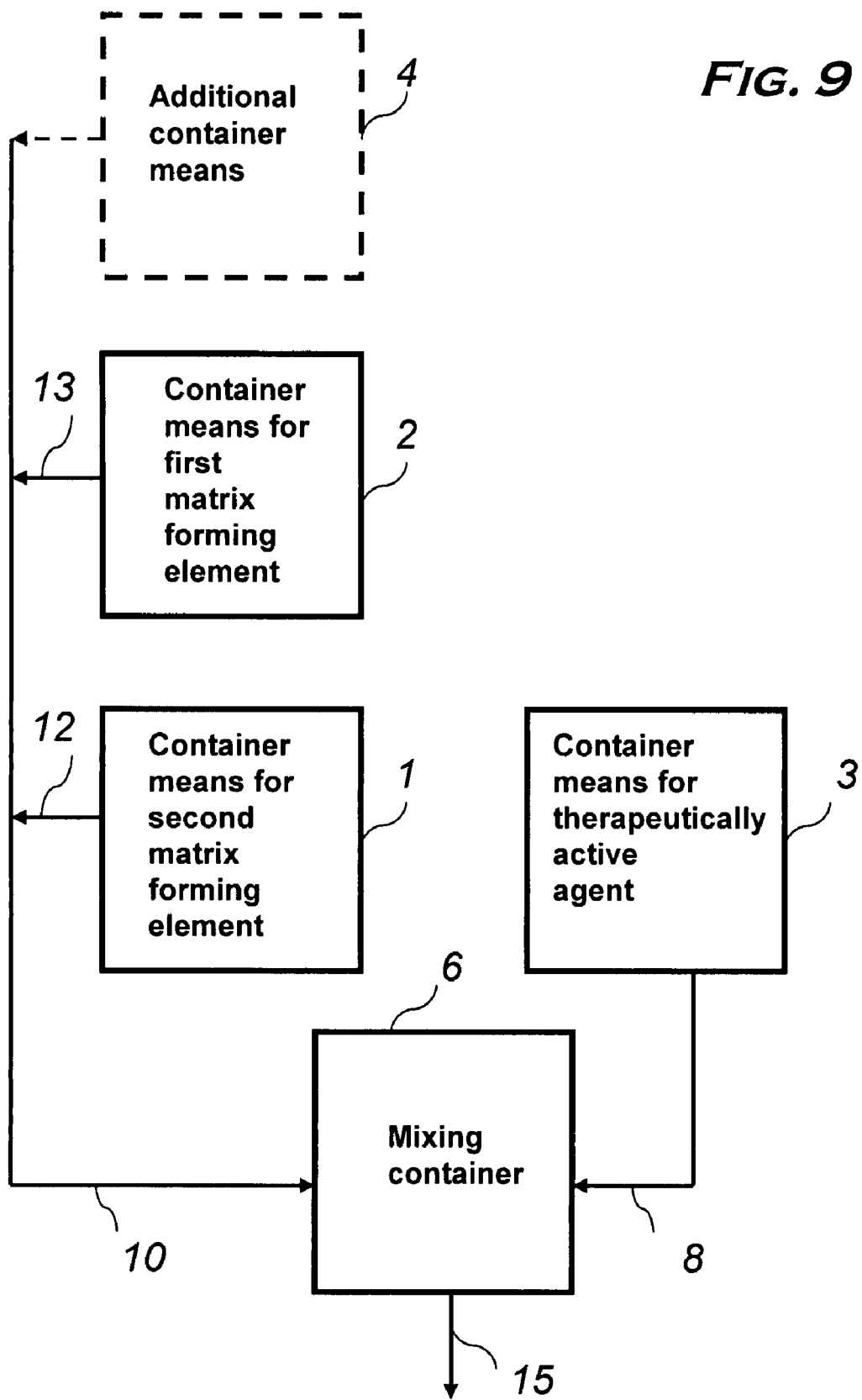

FIG. 7C Illustrates a comparison of fibrin, collagen, Gelfoam and Elvax methods of C3 delivery on long-distance regeneration. Animals were treated with the test delivery system without (−C3) or with (+C3) Rho antagonist. Distance of growth of the longest axon was scored by blind examination of at least five sections from each animal. The longest distance of axon growth was scored. Not shown here is that the animals that were not treated with Rho antagonist always showed axon retraction back from the site of lesion. When axon growth was measured, the distance was measured from the proximal edge of the lesion site. Each point represents data from one animal (approximately 5 sections per animal);

FIG. 8 Is Illustrative of open field test of behavioral recovery. Mice were scored for recovery of function by the 21 point BBB open field test (see experimental section). Two phase of recovery are seen. An early phase, observed in all mice, although the BBB score is higher in the C3-treated mice. The later phase of recovery of coordinated forelimb-hindlimb movement was only observed after treatment with C3. The C3-treated mice regain almost normal walking behavior; and FIG. 9 Is a schematic diagram of a system exploiting a kit in accordance with the present invention.

As used herein it is to be understood that a number of words and/or expressions are to have the meanings as hereinafter described.

The term "fibrin glue" or "fibrin clot" is meant to include any formulations used to make a fibrin clot: e.g. tisseel VH or see (Herbert (1998) J. Biomed. Mater. Res. 40:551-559, Cheng, et al. (1996) Science. 273:510-513, Guest (1997) J. Neurosci. Res. 50:888-905). Another definition is any fibrin glue composition not sold as Tisseel, but made by combining fibrinogen, thrombin calcium ions, with or without other components such as factor XIII or aprotinin.

The term "Rho antagonists" includes, but is not restricted to (known) C3, including C3 chimeric proteins, Y276321, or other Rho antagonists delivered in the delivery system.

The term "Y276321" is defined as a Rho kinase inhibitor that stimulated neurite outgrowth through its ability to inactive the Rho signaling pathway (Uehata, et al. (1997) Nature. 389:990-994, Bito (2000) Neuron. 26:431-441).

The term "nerve injury site" refers to a site of traumatic nerve injury or nerve injury caused by disease. The nerve injury site may be a single nerve (e.g. sciatic nerve) or a nerve tract comprised of many nerves (e.g. damaged region of the spinal cord). The nerve injury site may be in the central nervous system of peripheral nervous system in any region needing repair. The nerve injury site may form as a result of damage caused by stroke. The nerve injury site may be in the brain as a result of surgery, brain tumour removal or therapy following a cancerous lesion. The nerve injury site may result from Parkinson's disease, Alzheimer's disease, Amyotrophic lateral sclerosis, diabetes or any other type of neurodegenerative disease.

Rho GTPases include members of the Rho, Rac and Cdc42 family of proteins. Our invention concerns Rho family members of the Rho class. Rho proteins consist of different variants encoded by different genes. For example, PC12 cells express RhoA, RhoB and RhoC (Lehmann et al 1999 IBID). To inactivate Rho proteins inside cells, Rho antagonists of the C3 family type are effective because they inactivate all forms of Rho (e.g. RhoA, Rho B etc.). In contrast, gene therapy techniques, such as introduction of a dominant negative RhoA family member into a diseased cell, will only inactivate that specific RhoA family member.

Compounds of the C3 family from *Clostridium botulinum* inactivate Rho by ADP-ribosylation.

Recombinant C3 proteins, or C3 proteins that retain the ribosylation activity are also effective in our delivery system and are covered by this invention. In addition, Rho kinase is a well-known target for active Rho, and inactivating Rho kinase has the same effect as inactivating Rho, at least in terms of neurite or axon growth (Kimura and Schubert (1992) Journal of Cell Biology. 116:777-783, Keino-Masu, et al. (1996) Cell. 87:175-185, Matsui, et al. (1996) EMBO J. 15:2208-2216, Matsui, et al. (1998) J. Cell Biol. 140:647-657, Ishizaki (1997) FEBS Lett. 404:118-124), the biological activity that concerns this invention. Therefore, chemical compounds such as Y-27632, any other compound are covered by this invention as a preferred delivery in a tissue adhesive system. Numerous references describing C3 type compounds can be found in Methods in Enzymology, Vol. 256, Part B, Eds.: W. E. Balch, C. H. Der, and A. Hall; Academic Press, 1995, for e.g. Pgs. 196-206, 207 et seq, 184-189, and 174 et seq. In any event C3 may for example be selected from the group consisting of ADP-ribosyl transferase derived from *Clostridium botulinum* and a recombinant ADP-ribosyl transferase.

On the other hand any compound or molecule that does not have a direct action on Rho itself but works to decrease the function of Rho such as anti-sense oligos to Rho, anti-Rho kinase antibodies, and the like. Such Rho antagonists that can be delivered in a tissue adhesive system are also covered by our invention. The C3 polypeptides of the present invention include biologically active fragments and analogs of C3; fragments encompass amino acid sequences having truncations of one or more amino acids, wherein the truncation may originate from the amino terminus, carboxy terminus, or from the interior of the protein. Analogs of the invention involve an insertion or a substitution of one or more amino acids. Fragments and analogs will have the biological property of C3 that is capable of inactivation Rho GTPases. Also encompassed by the invention are chimeric polypeptides comprising C3 amino acid sequences fused to heterologous amino acid sequences. Said heterologous sequences encompass those which, when formed into a chimera with C3 retain one or more biological or immunological properties of C3. A host cell transformed or transfected with nucleic acids encoding C3 protein or c3 chimeric protein are also encompassed by the invention. Any host cell which produces a polypeptide having at least one of the biological properties of a C3 may be used. Specific examples include bacterial, yeast, plant, insect or mammalian cells. In addition, C3 protein may be produced in transgenic animals. Transformed or transfected host cells and transgenic animals are obtained using materials and methods that are routinely available to one skilled in the art. Host cells may contain nucleic acid sequences having the full-length gene for C3 protein including a leader sequence and a C-terminal membrane anchor sequence (see below) or, alternatively, may contain nucleic acid sequences lacking one or both of the leader sequence and the C-terminal membrane anchor sequence. In addition, nucleic acid fragments, variants and analogs which encode a polypeptide capable of retaining the biological activity of C3 may also be resident in host expression systems.

The Rho antagonist that is a recombinant proteins can be made according to methods present in the art. The proteins of the present invention may be prepared from bacterial cell extracts, or through the use of recombinant techniques. In general, C3 proteins according to the invention can be produced by transformation (transfection, transduction, or infection) of a host cell with all or part of a C3-encoding DNA fragment in a suitable expression vehicle. Suitable expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector.

Those skilled in the field of molecular biology will understand that any of a wide variety of expression systems can be used to provide the recombinant protein. The precise host cell used is not critical to the invention. The C3 protein can be produced in a prokaryotic host (e.g., *E. coli* or *B. subtilis*) or in a eukaryotic host (e.g., *Saccharomyces* or Pichia; mammalian cells, e.g., COS, NIH 3T3, CHO, BHK, 293, or HeLa cells; or insect cells).

Proteins and polypeptides can also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.). The methods of transformation or transfection and the choice of expression vehicle will depend on the host system selected.

The host cells harbouring the expression vehicle can be cultured in conventional nutrient media adapted as need for activation of a chosen gene, repression of a chosen gene, selection of transformants, or amplification of a chosen gene. One expression system is the mouse 3T3 fibroblast host cell transfected with a pMAMneo expression vector (Clontech, Palo Alto, Calif). pMAMneo provides an RSV-LTR enhancer linked to a dexamethasone-inducible MMTV-LTR promoter, an SV40 origin of replication which allows replication in mammalian systems, a selectable neomycin gene, and SV40 splicing and polyadenylation sites. DNA encoding a C3 protein would be inserted into the pMAMneo vector in an orientation designed to allow expression. The recombinant C3 protein would be isolated as described below. Other preferable host cells that can be used in conjunction with the pMAMneo expression vehicle include COS cells and CHO cells (ATCC Accession Nos. CRL 1650 and CCL 61, respectively).

C3 polypeptides can be produced as fusion proteins. For example, expression vectors can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Another strategy to make fusion proteins is to use the His tag system.

In an insect cell expression system, *Autographa californica* nuclear polyhedrosis virus AcNPV), which grows in *Spodoptera frugiperda* cells, is used as a vector to express foreign genes. A C3 coding sequence can be cloned individually into non-essential regions (for example the polyhedrin gene) of the virus and placed under control of an AcNPV promoter, e.g., the polyhedrin promoter. Successful insertion of a gene encoding a C3 polypeptide or protein will result in inactivation of the polyhedrin gene and production of non-occluded recombinant virus (i.e., virus lacking the proteinaceous coat encoded by the polyhedrin gene). These recombinant viruses are then used to infect *spodoptera frugiperda* cells in which the inserted gene is expressed (see, Lehmann et al for an example of making recombinant MAG protein).

In mammalian host cells, a number of viral-based expression systems can be utilised. In cases where an adenovirus is used as an expression vector, the C3 nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a C3 gene product in infected hosts.

Specific initiation signals may also be required for efficient translation of inserted nucleic acid sequences. These signals include the ATG initiation codon and adjacent sequences. In cases where an entire native C3 gene or cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, W138, and in particular, choroid plexus cell lines.

Alternatively, a C3 protein can be produced by a stably-transfected mammalian cell line. A number of vectors suitable for stable transfection of mammalian cells are available to the public; methods for constructing such cell lines are also publicly available. In one example, cDNA encoding the C3 protein can be cloned into an expression vector that includes the dihydrofolate reductase (DHFR) gene. Integration of the plasmid and, therefore, the C3 protein-encoding gene into the host cell chromosome is selected for by including 0.01-300 µM methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are known in the art; such methods generally involve extended culture in medium containing gradually increasing levels of methotrexate. DHFR-containing expression vectors commonly used for this purpose include pCVSEII-DHFR and pAdD26SV(A). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

A number of other selection systems can be used, including but not limited to the herpes simplex virus thymidine kinase, hypoxanthine-guanine phosphoribosyltransferase, and adenine phosphoribosyltransferase genes can be employed in tk, hgprt, or aprt cells, respectively. In addition, gpt, which confers resistance to mycophenolic acid; neo, which confers resistance to the aminoglycoside G-418; and hygro, which confers resistance to hygromycin can be used.

Alternatively, any fusion protein can be readily purified by utilising an antibody specific for the fusion protein being expressed. For example, a system described in Janknecht et al. (1981) Proc. Natl. Acad. Sci. USA 88, 8972, allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni2+ nitriloacetic acid-agarose columns, and histidine-tagged proteins are selectively eluted with imidazole-containing buffers.

Alternatively, C3 or a portion thereof, can be fused to an immunoglobulin Fc domain. Such a fusion protein can be readily purified using a protein A column.

It is envisioned that small molecule mimetics of the above described antagonists are also encompassed by the invention.

In the following a method to identify active Rho antagonists will be discussed.

To test Rho antagonists for activity, a tissue culture bioassay system was used. This bioassay is used to define activity of Rho antagonists that will be effective in promoting axon regeneration in spinal cord injury, stroke or neurodegenerative disease.

Neurons do not grow neurites on inhibitory myelin substrates. When neurons are placed on inhibitory substrates in tissue culture, they remain rounded. When an effective Rho antagonist is added, the neurons are able to grow neurites on myelin substrates. The time that it takes for neurons to growth neurites upon the addition of a Rho antagonist is the same as if neurons had been plated on growth permissive substrate such as laminin or polylysine, typically 1 to 2 days in cell culture. The results can be scored visually. If needed, a quantitative assessment of neurite growth can be performed. This involved measuring the neurite length in a) control cultures where neurons are plated on myelin substrates and left untreated b) in positive control cultures, such as neurons plated on polylysine c) or treating cultures with different concentrations of the test antagonist.

To test C3 in tissue culture, it has been found that the best concentration is 25-50 ug/ml. Thus, high concentrations of this Rho antagonist are needed as compared to the growth factors used to stimulate neurite outgrowth. Growth factors, such as nerve growth factor (NGF) are used at concentrations of 1-100 ng/ml in tissue culture. However, growth factors are not able to overcome growth inhibition by myelin. Our tissue culture experiments are all performed in the presence of the growth factor BDNF for retinal ganglion cells, or NGF for PC12 cells. When growth factors have been tested in vivo, typically the highest concentrations possible are used, in the ug/ml range. Also they are often added to the CNS with the use of pumps for prolonged delivery (e.g. Ramer et al, IBID). For in vivo experiments the highest concentrations possible was used when working with C3 stored as a frozen 1 mg/ml solution. The concentration that was chosen does not prevent the fibrin matrix from polymerizing.

For test purposes it was decided to dilute a 1 mg/ml solution of C3 with ⅓ volume thrombin and ⅓ volume fibrinogen solutions (contain calcium and aprotinin). In order to increase the concentration of C3, it would be possible to lyophylize C3 and then resuspend it in the fibrinogen solution. Lyophilized C3 has been tested and found to be active. The Rho antagonist C3 is stable at 37 C for at least 24 hours. The stability of C3 was tested in tissue culture with the following experiment. The C3 was diluted in tissue culture medium, left in the incubator at 37 C for 24 hours, then added to the bioassay system described above, using retinal ganglion cells as the test cell type. These cells were able to extend neurites on inhibitory substrates when treated with C3 stored for 24 hours at 37 C. Therefore, the minimum stability is 24 hours. This is in keeping with the stability projections based on amino acid composition (see sequence data, below).

In the following various tissue Adhesives and Formulations used to make them will be discussed.

Different types of tissue adhesive can be made. Examples include collagen gels, fibrin tissue adhesives. Other examples are matrigel, laminin networks, and adhesives based on a composition of basement membrane proteins that contain collagen.

Fibrin sealant has three basic components: fibrinogen concentrate, calcium chloride and thrombin. Other components can be added to affect the time of clot formation, and the size of the protein network that is formed. Generally when the components mix, a fibrin coagulum is formed in that the fibrinogen molecule is cleaved through the action of thrombin to form fibrin monomers which spontaneously will polymerize to form a three-dimensional network of fibrin, largely kept together by hydrogen bonding. This corresponds to the last phase of the natural blood clotting cascade, the coagulation rate being dependent on the concentration of thrombin used. In order to improve the tensile strength, covalent crosslinking between the fibrin chains is provided for by including Factor II in the sealant composition. In the presence of calcium ions, thrombin activates factor XIII to factor XIIIa. Activated factor XIIIa together with thrombin catalyzes the cross-linkage of fibrin and increases the strength of the clot. The strength of the fibrin clot is further improved by the addition of fibronectin to the composition, the fibronectin being crosslinked and bound to the fibrin network formed. During wound healing the clot material undergoes gradual lysis and is completely absorbed. To prevent a too early degradation of the fibrin clot by fibrinolys, the fibrin sealant composition may comprise a plasminogen activator inhibitor or a plasmin inhibitor, such as aprotinin. Such an inhibitor will also reduce the fibrinolytic activity resulting from any residual plasminogen in the fibrinogen composition. Similarly, compositions may include hyaluronic acid (or other polysaccharides), and these may also comprise a hyaluronidase inhibitor such as one or more flavonoids (or corresponding inhibitors for other polysaccharides) in order to prevent degradation (i.e. to prolong the duration) of the hyaluronic acid component by hyaluronidase which is always present in the surrounding tissues. The hyaluronic acid may, as mentioned above, be crosslinked, a commercially available example being Hylan.®™(trademark, available from Biomatrix, Ritchfield, N.Y., USA). The hyaluronic acid compositions may e.g. have the form of gels, solutions, etc.

Fibrin clots in any one of the above described embodiments, may be used for the application of a pharmaceutically active substance. By incorporating a drug, such as an antibiotic, a growth factor, etc. into the tissue adhesive it will be enclosed in the fibrin network formed upon application of the tissue adhesive. It will thereby be ensured that the drug is kept at the site of application while being controllably released from the composition.

Fibrin sealant products prepared from human plasma fibrinogen/Factor XIII are available commercially. One product is a tissue glue called Tisseel Fibrin Sealant (Baxter Hyland Immuno Corporation). (Tissucol/Tisseel, Immuno AG, Vienna) and another Beriplast P, Hoechst, West Germany. A frozen formulation of a fibrin glue delivered with a 2 syringe system is Hemaseel made by Hemacure Inc. (Kirkland, Quebec).

In the following methods for making Tissue Adhesive Delivery kits will be discussed.

In a preferred embodiment, the kit includes the solutions provided in separate bottles to prevent mixing before use, and an applicator designed so as to permit mixing of the fibrinogen/Factor XIII and thrombin with C3 at the body site. The kit would provide pre-measured amounts of the fibrinogen and factor XIII in one bottle, the thrombin in another bottle, a calcium chloride solution in third bottle, and a C3 solution in a fourth bottle. The contents of the bottles would be mixed in a prescribed order, as detailed in the example below. The kit can also include one or more other storage containers which are any necessary reagents including solvents, buffers, etc. The kit could be sold as lyophilized or frozen components to preserve the activity of C3 or other Rho antagonist added to the kit.

The applicator can, for example, take the form of a glass or plastic syringe with disposable needles. With a single syringe system, the components of the kit would be mixed immediately before application to the injury site.

A more elaborate system would allow two syringes to be attached, so that the mixing could take place in the syringe or a mixing compartment of the syringe, before injection. One example of a two syringe system is a Luer lock syringe, such as used for mixing adjuvants. For this a 3-way stopcocks, such as commercially available (Bio-Rad cat #7328103) is attached to the syringe so that the solution can be passed back and forth before attaching the injection needle to the third port of the 3-way stopcock. These are plastic, sterile, and disposable.

Another method of application could be through the use of a clip to hold two syringes, and the clip would have a common plunger to ensure that equal volumes of the thrombin and fibrinogen components are mixed in a chamber with the calcium chloride and C3, before being ejected trough the needle.

Other Ingredients for the Tissue Adhesive Rho Antagonist Delivery System are discussed hereinafter.

Other components can be added to the tissue adhesive to improve efficacy of the treatments. Such additions include growth factors, protease inhibitors, cytokines, anti-inflammatory compounds, cell transplant systems. Agents that prevent cell death, such as agents that affect the apoptosis pathway could be added components to the delivery system.

Methods of Packaging Delivery System are discussed hereinafter.

In the preferred formulation, Rho antagonist, fibrinogen and thrombin are mixed together just before application, so that polymerization of the gel occurs in the injured CNS. Therefore, it is important that the fibrinogen and thrombin are package separately. However, the C3 can be packaged separately, or added to either the thrombin or fibrinogen bottles. In another formulation, the fibrinogen, thrombin and C3 are packaged together, but help at low pH, which prevents polymerization of the gel. Polymerization would be induced by mixing this formulation with a basic component that would neutralize the pH to induce coagulation of the adhesive. In another formulation, the Rho antagonist could be added separately to the fibrinogen/thrombin mix in the form of liposomes or other similar delivery system. Living cells could that secrete C3 could be added as Rho antagonist.

A Method of Applying Rho Antagonist in Vivo is discussed hereinafter.

Tissue adhesive formulations are typically applied to wound sites with a syringe and needle. The shape of the need determine the type of surface that is formed when the adhesive polymerizes. In some cases, adhesives can be sprayed onto the wound surface, or into the desired region. This invention covers all types of syringes and needles used to apply fibrin plus Rho antagonists to injured regions of the CNS. In addition, it covers the addition of previously polymerized tissue adhesives with C3 to the wound. For example, fibrin can be polymerized in a teat tube, and forceps used to remove the gel and place it in the body cavity. Similarly, collagen can be applied by pre-polymerization and application by using forceps to place the gel in the injured spinal cord. One example of this is more fully explained in the example section of this application.

Tests were done with Gelfoam™, a surgical collagen-based sponge, and Elvax, a slow release plastic (Lehmann et al 1999, IBID) for the ability to deliver biologically effective concentrations of C3. Neither of these two delivery systems was effective. Therefore, only tissue adhesive formulations (i.e. the matrix forming formulations discussed herein) have efficacy in the delivery of C3 to the injured CNS in vivo.

Therapeutic Applications/Medical Uses will be discussed below.

The tissue adhesive system for the delivery of Rho antagonists may be useful in many other conditions that affect the central and peripheral nervous system. Treatments that are effective in eliciting sprouting from injured axons are equally effective in treating some types of stroke (Boston Life Sciences, Sep. 6, 2000 Press Release). Since it has been determined that it is possible to elicit sprouting (using a kit of the present invention), it is obvious that the treatments can be extended to stroke. Similarly, although the subject of this invention is related to delivery of Rho antagonists to the traumatically damaged nervous system, this invention also pertains to damage from neurodegeneration, such as during Parkinson's disease, Alzheimer's disease, prion diseases or other diseases of the CNS were axons are damaged in the CNS environment. In such cases, small volumes of the tissue adhesive with C3 could be injected into the affected region with the use of a syringe. The treatment will cause local sprouting to restore function of neurons whose axon processes had retracted in the course of the neurodegeneration.

Testing Example Formulation(s) and Delivery System(s) will be discussed below.

Tests of invention to formulation were conducted in mice after injury of the corticospinal tract. All mice were tested for anatomical regeneration of lesioned axons by anterograde tracing techniques. Some of the mice were also assessed for recovery of locomotion. The details of these experiments are given in the experimental section, the example sections, and the results are shown in the figures.

EXAMPLES

Example 1

A Kit for a Tissue Adhesive System.

The kit contains:
1 vial fibrinogen
1 vial aprotinin solution for reconstitution of fibrinogen
1 vial thrombin
1 vial calcium chloride solution for reconstitution of thrombin 1 vial C3 solution
1.1 Lyophilized fibrinogen (75 mg/ml) in glycine buffer (2 mg/ml NaCl, 4 mg/ml trisodium citrate, 15 mg/ml glycine) was reconstituted in an aprotinin solution 3000 KIU/ml and heated to 37 C. For ease of handling, a combined heating and stirring device was used (appropriate vials contain a magnetic stirrer. This is called solution I.
1.2 A thrombin solution is prepared; the solution comprising lyophilized thrombin 500 IU/ml, 2.4 mg/ml glycine, 8 mg/ml sodium chloride. The calcium chloride solution (40 umol $CaCl_2$) and thrombin are mixed and heated to 37 C. This is called solution II.
1.3 A solution of C3 (1 mg/ml) is heated to 37 C.
1.4 Equal amounts of solution I, II, and III are mixed, and immediately drawn up in a syringe, and added to the injury site where polymerization occurs. Thus the C3 is added as part of the fibrin glue solution that is placed in the lesion cavity to polymerize.

A combined heating and stirring device can be used in conjunction with the kit. For this, small magnetic stirrers are included in each of the mixing vials. The vials are then placed in the combined mixing and warming device where the magnetic stirrer keeps the solution stirred while the solution is warming.

Mice that received a dorsal hemisection were treated with the fibrin/C3 adhesive. In some experiments, 10 μl of 1 mg/ml C3 in phosphate buffered saline was added to the lesion site before applying the C3/fibrin. Behavior recovery was assessed in an open field environment as described by Beattie, Basso and Breshnahan (1995) J. Neurotrauma 12:1-20. Anatomical regeneration was assessed by anterograde labeling of the corticospinal fibres. Three weeks to three months after injury, the corticospinal fibres were labeled by inject the anterograde tracer WGA-HRP into the motor cortex as described in the art (Huang (1999) Submitted.). Two days later the animals were killed, the spinal cord removed, and longitudinal sections cut and reacted for HRP enzymatic activity, as described (Huang (1999) Submitted.). The labeled fibres were observed by microscopy to extend many mm past the lesion site (see FIGS. 5 and 6) after treatment with C3/fibrin.

Example 2

Modification of the Kit in Example 1

The formulation given in example 1 was used with the following modifications. Solution II is made with the addition of recombinant C3 directly to the solution II vial. In other words, solution II contains thrombin, calcium chloride and C3. Solution I is loaded in one syringe, solution II is loaded in a second syringe. A syringe with a plunger that simultaneously loads both solutions is used. Thus the solutions are mixed as they enter a small chamber before the needle, and the polymerization occurs in situ in the injured region of the CNS where the solution is applied. The system describe here is the Duploject system from Baxter Pharmaceuticals U.S.A.

Example 3

Modification of the Kit in Example 1

As example 2, but the C3 solution is mixed in vial I with the fibrinogen. Vial one and vial II are heated and prepared as described in example 1, and injected into the injured CNS with the Duploject system.

Example 4

Collagen Gels Used as Tissue Adhesives

First collagen is purified. Collagen can be purified from any source, human or mammalian. One source of collagen is the EHS tumor cell line which is passed in mice. Collagen was purified from rat tails. The tails were soaked in 70% alcohol for about 20 minutes. The remaining steps were performed under aseptic conditions. The tails are broken about 2 cm from the tip with a hemostat and the tendon is slowly pulled out and placed in a sterile dish. The tendons are cut into small pieces and soaked in acetic acid-water (1:1000) for 48 hours in the cold. 150 ml of solution is used per tail. The solution is centrifuged at 15,000 rpm, 30 min. and stored in aliquots at B10C.

Collagen gels with C3 as Rho antagonist are formed in vivo as follows. For treatment of one mouse, 40 μg of C3 was lyophilized. The C3 protein was reconstituted in 10 μl of 7.5% $NaHCO_3$. Collagen at 0.7 mg/ml was used, and 25 μl collagen was added to the C3 solution. A mouse that had received a dorsal hemisection of the spinal cord was treated with 10 μl of 1 mg/ml C3 in the collagen (i.e. at the lesion site). The time it takes for the collagen to polymerize may be modified by varying the $NaHCO_3$ solution. Anatomical regeneration of transected cortical spinal fibres was assessed as described in the detailed description of the invention.

Example 5

Procedure to Make Recombinant C3 as a Rho Antagonist

Recombinant C3 protein was made as follows. The plasmid pGEX2T-C3 coding for the glutathione-S-transferase (GST)-C3 fusion protein was obtained from N. Lamarche (McGill Univ.). Bacteria were transformed with pGEX2T-C3, allowed to grow overnight induced with IPTG, and sonicated to break open the cells. The recombinant protein was purified by affinity chromatography as described (Ridley and Hall (1992) Cell. 70:389-399). The GST fusion protein was cleaved by thrombin, and thrombin was removed by incubation with 100 μl of p-aminobenzamidine agarose-beads (Sigma). The C3 solution was dialyzed against PBS, and sterilized with a 0.22 μm filter. The C3 concentration was evaluated by protein assay (DC assay, BioRad Labs, Missassauga, Ont.) and C3 purity was controlled by SDS-PAGE analysis.

Example 6

Testing the Fibrin-Rho-Antagonist Formulation Using the Delivery System

To test the tissue adhesive system a rodent model of spinal cord injury was used. For this, Balb-c mice were anesthetized with 0.6 ml/kg hypnorm, 2.5 mg/kg diazepam and 35 mg/kg ketamine. A section of the thoracic spinal cord was exposed using fine rongers to remove the bone. A dorsal hemisection was made to cut the dorsal columns at level T6. The fibrin/C3 adhesive was injected immediately after injury. As control another group of animals received fibrin alone, and a third group received no treatment. The following day behavioural testing began, and continued for three weeks. The animals were placed in an open field environment that consisted of a rubber mat approximately 4'×3' in size. The animals were left to move randomly, the movement of the animals were videotaped. For each test two observers scored the animals for ability to move ankle, knee and hip joints in the early phase of recovery. In the intermediate phase, the ability to support weight and correct placement of the feet was assessed (dorsal or plantar placement). In the late phase of recovery, the animals were assessed for correct foot position, trunk stability, and foot drag. Only animals that received C3/fibrin reached the late phase of recovery of coordinated forelimb-hindlimb movement. Untreated control animals did not typically pass beyond the early phase of recovery.

Additional experimental activity will be discussed below.

Spinal Cord Injury

To study The CST was cut bilaterally by a dorsal hemisection extending past the central canal (1 (FIG. 2) at the T6 level. Balb-c mice were anesthetized with 0.6 ml/kg hypnorm, 2.5 mg/kg diazepam and 35 mg/kg ketamine. A section of the thoracic spinal cord was exposed using fine rongers to remove the bone, and a dorsal hemisection was made at level T6. Fine scissors were used to cut the dorsal half of the spinal cord, and it was recut a second time with fine knife to ensure all lesions extended past the central canal. Three weeks to four weeks after injury, the corticospinal fibres were labeled by injection the anterograde tracer WGA-HRP into the motor cortex as into 6 sites. For injection into the motor cortex a pulled glass pipette was used. Two days later the animals were perfused transcardially with saline then 4% paraformaldehyde and the spinal cords and brains were removed.

C3 toxin was delivered locally to the site of the lesion by a fibrin-based tissue adhesive delivery system (FIG. 1). Recombinant C3 was mixed with fibrinogen and thrombin in the presence of $CaCl_2$. Fibrinogen is cleaved by thrombin, and the resulting fibrin monomers polymerize into a three-dimensional matrix. C3 was added as part of a fibrin adhesive, which polymerized within about 10 seconds after being placed in the injured spinal cord. Anterograde tracing with WGA-HRP was used to study anatomical regeneration past the site of lesion in three groups of animals: animals treated with fibrin plus C3 (C3/fibrin), animals treated with fibrin alone, and animals that did not received treatment after injury (see FIG. 7). With no treatment, transected CST axons retract back from the site of lesion from 500 um to 1 mm (FIG. 3). Animals treated with fibrin alone showed less axon retraction, and sprouting of axons was observed to extend towards the scar. Application of C3 to the injured spinal cord elicited an extensive sprouting of CST axons into the dorsal white matter, and the axons grew into the scar and extended past the lesion (FIG. 4). A long distance regeneration of individual CST axons and axon bundles was elicited by C3 (FIG. 5), but not in untreated or fibrin controls. This regeneration was significantly different from any growth observed following treatment with fibrin alone.

Several different tissue adhesive delivery systems were tested. When C3 was delivered in collagen gels less axon retraction was observed, but the same extent of axon regeneration was not observed as with fibrin. Gelfoam™, a surgical collagen sponge, was also tested. Gelfoam was not as effective as fibrin as promoting long-distance regeneration (FIG. 7). A non-biological material, Elvax, was also tested which is a polymer-based artificial release system (see Lehmann et al, 1999 IBID.). This system was not effective in allowing cut axons access to C3.

To test functional recovery following treatment of injured spinal cord with C3, three groups of animals were score for locomotor behaviour in an open field environment according to the 21 point BBB scale (Basso et al. ). The animals were examined by two reviewers and were placed alone in an open field environment that consisted of a rubber mat approximately 4'×3' in size. Each animal was videotaped for approx. 3 min. For the early and intermediate phases, the BBB scores were derived following observation, and confirmed by video analysis. In the late phase of recovery, the BBB score was determined from the videos projected on a computer at 3 speed from sequences of 4 steps or more. The BBB test includes three phases of recovery: an early phase (scores 1-7) of joint movement, an intermediate phase (score 8-13) where weight support and foot placement (dorsal or plantar) are assessed, and a late phase of coordinated movements (scores 14-21) where correct foot position, and foot drag are examined. The C3 treated animals rapidly regained the ability to support weight (FIG. 7B) while control animals moved mostly by the action of their forelimbs (FIG. 7A). The control groups entered the intermediate recovery phase with the ability to support weight within one weeks, at which point they obtained their recovery plateau. Animals that received C3 treatment continues to recover over the 1 month period of observation, and recovered coordinated movement and almost normal stepping (FIG. 8).

In rats that receive a contusion injury the recovery period depends on the severity and location of the lesion. Typically, rats reach a plateau of recovery by about two week, whereas after dorsal hemisection in mice it was found that the plateau of recovery is reached within about 1 week. The remarkable improvement in C3-treated mice within one day of spinal cord lesion is likely due to changes in the local spinal cord circuitry. These local changes might result from the robust sprouting immediately after application of C3 is applied to the transected axons. Rates of axon growth in vivo are known to be approximately the same as the slow axonal transport rate of 50-200 um/hr. It is also possible that the local effects on the spinal cord are mechanistically different by acting on central pattern generators implicated in walking behaviors or by neuroprotection immediately after treatment. Most importantly, treated mice performed better immediately after lesion, and they recovered almost normal walking patterns by one month (FIG. 8). This slower phase of recovery is attributed to the long-distance regeneration of axons that was induced by C3 (FIG. 4). Moreover, while we only flowed the CST axons in this study, our treatments also are likely stimulate growth from other transected axonal populations.

In the following Production of Recombinant C3 will be discussed.

C3 is a protein product made by the bacteria *Clostridium botulinum*. The fragment containing the C3 gene was cloned into a pGEX vector (from Amersham Pharmacia Biotech inc. Baie D'rfe, Quebec, Canada), now referred to as pGEX2T-C3, and this vector was obtained from Nathalie Lamarche of McGill University. To confirm the C3 sequence corresponded to that reported in the literature the insert was sequenced (see sequence below). The C3—containing pGEX vector was transformed into the RR1 strain of *E. coli* (GIBCO).

Bacteria were grown in L-Broth (10 g/L Bacto-Tryptone, 5 g/L Yeast Extract, 10 g/L NaCl (Fisher Scientific) with Ampicillin(BMC-Roche) at 50 ug/ml in a shaking incubator for 1 hr at 37° C. Isopropyl β-D-thiogalactopyranoside(IPTG), (GIBCO) was added to a final concentration of 0.5 mM to induce production of recombinant protein and the culture was grown for a further 6 hrs at 37 C. Bacterial pellets were obtained by centrifugation, in 250 ml centrifuge bottles, at 6000 rpm at 4° C. for 5 min. Pellets can be kept frozen at −80° C. at this time.

5 mls of Buffer A(50 mM Tris, pH7.5, 50 mM NaCl, 5 mM $MgCl2$, 1 mM DTT)+1 mM PMSF was added to each pellet. Pellets were resuspended and transferred to a 50 ml plastic beaker on ice, and a further 5 mls of buffer A was used to wash the centrifuge bottles. Total volume of buffer A+pellets from a 2 L culture is usually 30-40 mls. The pellets, on ice, were sonicated 5×30 secs using a BRANSON SONIFIER 450 probe sonicator. Bacteria were cooled on ice 1 minute between sonications. The sonicate was centrifuged in a Sorvall SS-34 rotor at 10,000 rpm for 10 min at 4 C to clarify supernatant.

Glutathione-agarose beads (SIGMA#G-4510) were purchased as a lyophilized powder and the beads were swollen in deionized water, then stored in 1M NaCl at 4° C. Five ml of the beads (50% v/v) were washed in a 50 ml tube filled with buffer A (no PMSF). Tube was centrifuged at 2000 rpm (500 g) for 5 min, water was removed, and replaced with buffer A. These beads were added to the cleared bacterial supernatant, and mixed for 1-2 hrs at 4 C. The beads were washed 4 times with buffer B (buffer A, NaCl is 150 mM, no PMSF), then 2× with buffer C (buffer B+2.5 mM $CaCl_2$). Washes were poured out and the beads retained each time. Next, 5 mls of thrombin (Bovine, Plasminogen-free, CALBIOCHEM #605160) 20 U at (50% v/v) was added to the beads to cleave the C3 from the GST affinity purification tag (see cleavage site in the nucleotide sequence given below). This reaction was left overnight, with mixing, at 4° C.

The beads are loaded into an empty 10 ml column, PBS (phosphate buffered saline) was added to the column and 20 1 ml aliquots were collected. To determine the location of the protein peak, 0.5 µl spots were put on a nitrocellulose sheet, from each aliquot, and this is stained with Amido Black(Biorad) as a protein dot-blot. Aliquots containing C3 were pooled and 20 ul p-Aminobenzamidine (SIGMA#A7155) was added. The solution was mixed for 30 min at 4 C to remove the thrombin. The C3 is centrifuged to remove the p-aminobenzamidine, and then concentrated using a CENTRIPREP-10 concentrator (AMICON). The concentrated C3 is then passed through a PD-10 column (PHARMACIA, containing Sephadex G-25M) and 100.5 ml aliquots are collected. A dot-blot is done on these aliquots, and the appropriate aliquots (usually 3 tubes) are pooled (total volume about 1.5 mls). The purified recombinant protein was filter-sterilized, aliquoted, and stored at 80° C. A protein assay was done on a small amount to determine precisely the concentration. Purity of the recombinant C3 was evaluated by SDS polyacrylamide gel electrophoresis. Bioactivity was assessed with a bioassay using either retinal ganglion cells or PC12 cells (see identification of Rho antagonist section).

SEQUENCE of (known) Rho Antagonist C3 Used in the Experiments

Nucleotide sequence including part of the plasmid GST sequence. The vector with the GST sequence is commercially available and thus the entire GST sequence including the start was not sequenced. It was desired to determine only the sequence 3' to the thrombin cleavage site which releases C3 from the GST sequence. The thrombine cleavage site is shown with an arrow and is located just to the left of the underlined nucleotide sequence below (i.e. the arrow shows the thrombin cleavage site). The underlined sequence shows additional coding sequence translated in our recombinant protein that is not reported in the literature.

Both strands were sequenced to verify that there were no errors in the sequence.

```
                                                              ↓
5' GTG GCG ACC CTT CCC AAA TCG GAT CTG GTT CCG CGT GGA TCC TCT AGA

GTC GAC CTG CAG GCA TGC AAT GCT TAT TCC ATT AAT CAA AAG GCT TAT

TCA AAT ACT TAC CAG GAG TTT ACT AAT ATT GAT CAA GCA AAA GCT TGG

GGT AAT GCT CAG TAT AAA AAG TAT GGA CTA AGC AAA TCA GAA AAA GAA

GCT ATA GTA TCA TAT ACT AAA AGC GCT AGT GAA ATA AAT GGA AAG CTA

AGA CAA AAT AAG GGA GTT ATC AAT GGA TTT CCT TCA AAT TTA ATA AAA

CAA GTT GAA CTT TTA GAT AAA TCT TTT AAT AAA ATG AAG ACC CCT GAA

AAT ATT ATG TTA TTT AGA GGC GAC GAC CCT GCT TAT TTA GGA ACA GAA

TTT CAA AAC ACT CTT CTT AAT TCA AAT GGT ACA ATT AAT AAA ACG GCT

TTT GAA AAG GCT AAA GCT AAG TTT TTA AAT AAA GAT AGA CTT GAA TAT

GGA TAT ATT AGT ACT TCA TTA ATG AAT GTT TCT CAA TTT GCA GGA AGA

CCA ATT ATT ACA AAA TTT AAA GTA GCA AAA GGC TCA AAG GCA GGA TAT

ATT GAC CCT ATT AGT GCT TTT CAG GGA CAA CTT GAA ATG TTG CTT CCT

AGA CAT AGT ACT TAT CAT ATA GAC GAT ATG AGA TTG TCT TCT GAT GGT

AAA CAA ATA ATA ATT ACA GCA ACA ATG ATG GGC ACA GCT ATC AAT CCT

AAA TAA 3'
```

Neucleotide sequence of recombinant C3 protein: the sequence given below represents the entire coding sequence for the Rho antagonist used in the experiments mentioned herein. It is similar to the sequence shown above but does not include the GST portion which when the protein is made is enzymatically removed with thrombin.

```
  1 GGATCCTCTA GAGTCGACCT GCAGGCATGC AATGCTTATT CCATTAATCA

51 AAAGGCTTAT TCAAATACTT ACCAGGAGTT TACTAATATT GATCAAGCAA

101 AAGCTTGGGG TAATGCTCAG TATAAAAAGT ATGGACTAAG CAAATCAGAA

151 AAAGAAGCTA TAGTATCATA TACTAAAAGC GCTAGTGAAA TAAATGGAAA

201 GCTAAGACAA AATAAGGGAG TTATCAATGG ATTTCCTTCA AATTTAATAA

251 AACAAGTTGA ACTTTTAGAT AAATCTTTTA ATAAAATGAA GACCCCTGAA

301 AATATTATGT TATTTAGAGG CGACGACCCT GCTTATTTAG GAACAGAATT

351 TCAAAACACT CTTCTTAATT CAAATGGTAC AATTAATAAA ACGGCTTTTG

401 AAAAGGCTAA AGCTAAGTTT TTAAATAAAG ATAGACTTGA ATATGGATAT

451 ATTAGTACTT CATTAATGAA TGTTTCTCAA TTTGCAGGAA GACCAATTAT

501 TACAAAATTT AAAGTAGCAA AAGGCTCAAA GGCAGGATAT ATTGACCCTA

551 TTAGTGCTTT TCAGGGACAA CTTGAAATGT TGCTTCCTAG ACATAGTACT

601 TATCATATAG ACGATATGAG ATTGTCTTCT GATGGTAAAC AAATAATAAT

651 TACAGCAACA ATGATGGGCA CAGCTATCAA TCCTAAATAA
```

Amino Acid Sequence (One Letter Code)

Translation of the above sequence to show amino acid sequence. Amino acids in bold, highlight differences from published sequence (Popoff et al. (1990) Nucl. Acid. Ress. 18:1291. EMBL accession no. X511464). The 11 N-terminal sequences are additional; there is a single amino acid change of an alanine (hydrophobic) to glutamic acid (Q).

```
GSSRVDLQAC NAYSINQKAY SNTYQEFTNI DQAKAWGNAQ

YKKYGLSKSE KEAIVSYTKS ASEINGKLRQ NKGVINGFPS

NLIKQVELLD KSFNKMKTPE NIMLFRGDDP AYLGTEFQNT

LLNSNGTINK TAFEKAKAKF LNKDRLEYGY ISTSLMNVSQ

FAGRPIITKF KVAKGSKAGY IDPISAFQGQ LEMLLPRHST

YHIDDMRLSS DGKQIIITAT MMGTAINPK
```

Number of amino acids: 229
Molecular weight: 25507.5
Theoretical pI: 9.43
Amino acid composition:

| | | |
|---|---|---|
| Ala (A) | 18 | 7.9% |
| Arg (R) | 7 | 3.1% |
| Asn (N) | 18 | 7.9% |
| Asp (D) | 10 | 4.4% |
| Cys (C) | 1 | 0.4% |
| Gln (Q) | 12 | 5.2% |
| Glu (E) | 10 | 4.4% |
| Gly (G) | 16 | 7.0% |
| His (H) | 2 | 0.9% |
| Ile (I) | 18 | 7.9% |
| Leu (L) | 17 | 7.4% |
| Lys (K) | 24 | 10.5% |
| Met (M) | 7 | 3.1% |
| Phe (F) | 10 | 4.4% |
| Pro (P) | 7 | 3.1% |
| Ser (S) | 20 | 8.7% |
| Thr (T) | 14 | 6.1% |
| Trp (W) | 1 | 0.4% |
| Tyr (Y) | 11 | 4.8% |
| Val (V) | 6 | 2.6% |
| Asx (B) | 0 | 0.0% |
| Glx (Z) | 0 | 0.0% |
| Xaa (X) | 0 | 0.0% |

Total number of negatively charged residues (Asp+Glu): 20
Total number of positively charged residues (Arg+Lys): 29

Estimated Half-life:
The N-terminal of the sequence considered is G (Gly).
The estimated half-life is: 30 hours (mammalian reticulocytes, in vitro).
>20 hours (yeast, in vivo).
>10 hours (*Escherichia coli*, in vivo).

Instability Index:
The instability index (II) is computed to be 26.88
This classifies the protein as stable.
Aliphatic index: 75.07
Grand average of hydropathicity (GRAVY): −0.479

Turning now to FIG. 9, this figure illustrates in schematic fashion a system exploiting a kit of the present invention for mixing and delivering a supplemented matrix forming material. An actual apparatus may for example be of multi-cartridge syringe type as known or modified as necessary or desired.

The kit portion of the illustrated system comprises a container means 1 for fibrinogen material, a container means 2 for thrombin material and a container means 3 for a therapeutically active agent for facilitating axon growth (e.g. C3 or a modified or hybrid C3). If desired or necessary the kit portion may include additional containers for the separate containment of other desired or necessary components; as shown the system in FIG. 9 includes in dotted outline an additional container means 4 for the flowable matrix forming part of the kit. The system also includes a mixing container 6 wherein the C 3 (hybrid) is mixed with the matrix forming elements to form the supplemented flowable matrix forming carrier. The feed line 8 is indicative of the addition of C3 to the container 6 whereas the feed line 10 is indicative of the addition of the flowable matrix forming elements from containers 1 and 2 and which is formed from the merging of feed lines 12 and 13. The mixing in the container means 6 may be effected or carried out in any suitable (known) fashion, (e.g. simple stirring with a magnetic stirrer). The output line 15 of the mixing container is indicative of the delivery of the supplemented mixture to the lesion site (e.g. by needle (e.g. syringe), pipette, etc.

Although in FIG. 9 the therapeutically active agent for facilitating axon growth (e.g. C3) is shown as being associated with a separate container means 3, if so desired or as necessary the therapeutically active agent may be associated with a container holding a flowable carrier component (e.g. a container may hold fibrinogen and C3).

I claim:

1. An axon sprouting stimulation kit comprising
a first container comprising a flowable collagen matrix,
a second container comprising a matrix-releasable therapeutically active agent,
a mixing means for intermingling the flowable collagen matrix and the matrix-releasable therapeutically active agent into a therapeutically acceptable matrix, and;
a delivery means,
wherein the matrix-releasable therapeutically active agent is selected from the group consisting of C3 and Y-27632 for facilitating axon sprouting at a nerve lesion site.

2. The axon sprouting stimulation kit of claim 1, wherein C3 is selected from the group consisting of ADP-ribosyl transferase C3 derived from *Clostridium botulinum* and a recombinant C3 retaining ADP-ribosylation activity.

3. The axon sprouting stimulation kit of claim 1, further comprising a protease inhibitor.

4. The axon sprouting stimulation kit of claim 3, wherein said protease inhibitor is aprotinin.

5. The axon sprouting stimulation kit of claim 3, wherein C3 is selected from the group consisting of ADP-ribosyl transferase C3 derived from *Clostridium botulinum* and a recombinant C3 retaining ADP-ribosylation activity.

6. An axon sprouting stimulation kit comprising
a container comprising a flowable collagen matrix and a matrix-releasable therapeutically active agent, and;
a delivery means,
wherein the matrix-releasable therapeutically active agent is selected from the group consisting of C3 and Y-27632 for facilitating axon sprouting at a nerve lesion site.

7. The axon sprouting stimulation kit of claim 6, wherein C3 is selected from the group consisting of ADP-ribosyl transferase C3 derived from *Clostridium botulinum* and a recombinant C3 retaining ADP-ribosylation activity.

8. The axon sprouting stimulation kit of claim 6, further comprising a protease inhibitor.

9. The axon sprouting stimulation kit of claim 8, wherein said protease inhibitor is aprotinin.

10. The axon sprouting stimulation kit of claim 8, wherein C3 is selected from the group consisting of ADP-ribosyl transferase C3 derived from *Clostridium botulinum* and a recombinant C3 retaining ADP-ribosylation activity.

11. A biocompatible composition for facilitating axon sprouting, said composition comprising: (i) a therapeutically active agent selected from the group consisting of C3 and Y-27632 for facilitating axon sprouting, and (ii) a flowable collagen matrix.

12. The biocompatible composition of claim 11, wherein C3 is selected from the group consisting of ADP-ribosyl transferase C3 derived from *Clostridium botulinum*, and a recombinant C3 retaining ADP-ribosylation activity.

* * * * *